US011185253B2

(12) United States Patent
Anderson et al.

(10) Patent No.: US 11,185,253 B2
(45) Date of Patent: *Nov. 30, 2021

(54) PATTERN RECOGNITION SYSTEM FOR QUANTIFYING THE LIKELIHOOD OF THE CONTRIBUTION OF MULTIPLE POSSIBLE FORMS OF CHRONIC DISEASE TO PATIENT REPORTED DYSPNEA

(71) Applicant: Shape Medical Systems, Inc., St. Paul, MN (US)

(72) Inventors: Stephen T. Anderson, North Oaks, MN (US); Dean J. MacCarter, Englewood, CO (US); David M. Anderson, White Bear Lake, MN (US); Andrew Hofmeister, Moraga, CA (US)

( * ) Notice: Subject to any disclaimer, the term of this patent is extended or adjusted under 35 U.S.C. 154(b) by 458 days.

This patent is subject to a terminal disclaimer.

(21) Appl. No.: 16/011,627

(22) Filed: Jun. 18, 2018

(65) Prior Publication Data

US 2018/0296127 A1   Oct. 18, 2018

Related U.S. Application Data

(63) Continuation of application No. 14/341,442, filed on Jul. 25, 2014, now Pat. No. 10,010,264.

(Continued)

(51) Int. Cl.
*A61B 5/08*   (2006.01)
*A61B 5/083*   (2006.01)
(Continued)

(52) U.S. Cl.
CPC .......... *A61B 5/0826* (2013.01); *A61B 5/0833* (2013.01); *A61B 5/0836* (2013.01);
(Continued)

(58) Field of Classification Search
CPC ......... A61B 5/08; A61B 5/0816; A61B 5/082; A61B 5/083; A61B 5/0826; A61B 5/087
See application file for complete search history.

(56) References Cited

U.S. PATENT DOCUMENTS

| 4,463,764 A | 8/1984 | Anderson et al. |
| 5,398,695 A | 3/1995 | Anderson et al. |
| (Continued) | | |

FOREIGN PATENT DOCUMENTS

| CN | 101524274 | 9/2009 |
| CN | 103153184 | 6/2013 |

OTHER PUBLICATIONS

Office Action for Chinese Application No. 201580028147.4, dated Dec. 4, 2018 along with English translation, 18 pages.
(Continued)

*Primary Examiner* — Puya Agahi
(74) *Attorney, Agent, or Firm* — Wallenfelt Law PLC

(57) ABSTRACT

Systems and methods for quantifying the likelihood of the contribution of multiple possible forms of chronic disease to patient reported dyspnea can include the testing protocol having a flow/volume loop, performed at rest, flowed by the measurement of cardiopulmonary exercise gas exchange variables during rest, exercise and recovery as unique data sets. The data sets are analyzed using feature extraction steps to produce a pictorial image consisting of disease silos displaying the likelihood of the contribution of various chronic diseases to patient reported dyspnea. In some embodiments, the silos are split into subclass silos. In some embodiments, multiple chronic disease indexes are used to differentiate between sub-types of a particular chronic disease (e.g., differentiating WHO 1 PH from WHO 2 or WHO (Continued)

3 PH). Test results are plotted serially to asses to provide feedback to the physician on the efficacy of therapy provided to the patient.

22 Claims, 18 Drawing Sheets

Related U.S. Application Data

(60) Provisional application No. 61/858,140, filed on Jul. 25, 2013, provisional application No. 61/971,915, filed on Mar. 28, 2014.

(51) Int. Cl.
    *A61B 5/087*     (2006.01)
    *A61B 5/00*     (2006.01)
    *A61B 5/091*     (2006.01)

(52) U.S. Cl.
    CPC .............. *A61B 5/0002* (2013.01); *A61B 5/087* (2013.01); *A61B 5/0816* (2013.01); *A61B 5/091* (2013.01); *A61B 5/742* (2013.01); *A61B 5/7475* (2013.01)

(56) References Cited

U.S. PATENT DOCUMENTS

| | | | |
|---|---|---|---|
| 5,502,660 A | 3/1996 | Anderson et al. | |
| 5,925,831 A | 7/1999 | Storsved | |
| 6,089,105 A | 7/2000 | Ricciardelli | |
| 6,358,215 B1 | 3/2002 | Ricciardelli | |
| 6,659,962 B2 | 12/2003 | Ricciardelli | |
| 7,225,022 B2 | 5/2007 | Anderson et al. | |
| 7,713,211 B2 | 5/2010 | Anderson et al. | |
| 7,878,980 B2 | 2/2011 | Ricciardelli | |
| 8,342,178 B2 | 1/2013 | Hengstenberg et al. | |
| 8,459,261 B2 | 6/2013 | Ricciardelli et al. | |
| 8,460,203 B2 | 6/2013 | Ricciardelli | |
| 8,630,811 B2 | 6/2014 | Anderson et al. | |
| 8,768,463 B2 | 7/2014 | Anderson et al. | |
| 8,775,093 B2 | 7/2014 | Anderson et al. | |
| 2002/0185131 A1 | 12/2002 | Madaus et al. | |
| 2004/0017475 A1 | 1/2004 | Akers et al. | |
| 2004/0186389 A1 | 9/2004 | Mault et al. | |
| 2005/0115561 A1 | 6/2005 | Stahmann et al. | |
| 2009/0076347 A1 | 3/2009 | Anderson et al. | |
| 2009/0281443 A1 | 11/2009 | Hengstenberg et al. | |
| 2011/0208082 A1 | 8/2011 | Madaus et al. | |
| 2012/0130265 A1 | 5/2012 | Cha et al. | |
| 2013/0324873 A1 | 12/2013 | Babaeizadeh et al. | |
| 2013/0345572 A1 | 12/2013 | Karbing et al. | |
| 2014/0163397 A1 | 6/2014 | Anderson et al. | |

OTHER PUBLICATIONS

Arena et al., "The partial pressure of resting end-tidal carbon dioxide predicts major cardiac events in patients with systolic heart failure," Am Heart J 2008;156:982-88.

Arena et al., "Ventilatory Expired Gas at Low-Intensity Exercise Predicts Adverse Events and Is Related to Neurohormonal Markers in Patients with Heart Failure," J Card Fail Aug. 2009;15(6):482-8. Epub Feb. 10, 2009.

Beaver et al.,"On-line computer analysis and breath-by-breath graphical display of exercise function tests," Journal of Applied Physiology, vol. 34, No. 1, Jan. 1973.

Froelicher et al., "Exercise and the Heart," Mosby-Year Book, Inc. 1993, p. 38.

Gaine et al., "Primary Pulmonary Hypertension," Lancet 1998; 352: 719-25.

Guazzi et al., "Ventilatory Efficiency and Dyspnea on Exertion Improvements are Related to Reduced Pulmonary Pressure in Heart Failure Patients Receiving Sildenafil," Int J Cardiol. Mar. 27, 2009. [Epub ahead of print] PMID: 19329196.

Kim et al., "A Multivariable Index (MVI) for Grading Exercise Gas Exchange Severity in Patients with Pulmonary Arterial Hypertension and Heart Failure," Pulmonary Medicine, vol. 2012, Article ID 962598, doi:10.1155/2012/962598 (2012).

Marieb, "Human Anatomy and Physiology," Benjamin/Cummings Publishing Company, 1992, p. 749.

Yasunobu et al., "End-tidal PCO2 Abnormality and Exercise Limitation in Patients with Primary Pulmonary Hypertension," Chest 2005; 127:1637-1646.

International Search Report and Written Opinion for Application No. PCT/US2015/020703 dated Jul. 13, 2015.

Figure 2

| Key | Test Key | Phase | Breath Count | PetCO2 | VCO2 | VO2 | VT | Heart Rate | RR | Bar. Press. | ... |
|---|---|---|---|---|---|---|---|---|---|---|---|
| 386 | 327 | Rest | data | data | data | data | data | data | data | data | data |
| 387 | 327 | Exercise | data | data | data | data | data | data | data | data | data |
| 388 | 327 | Recovery | data | data | data | data | data | data | data | data | data |

154 → Key
156 → Test Key
158 → Phase
152 (bracket around 386, 387, 388)
160 (bracket around data columns)
150 (overall table)

Figure 10

| | Deconditioned | Obesity | Heart | Vascular | Obstructive Lung | Restrictive Lung |
|---|---|---|---|---|---|---|
| Shape Score (MVi) | | | | | | |
| MPiph | x | | | | | |
| VE/VCO2 slope | | | x | x | | |
| OUES | | | | | | |
| VE/HR slope | x | | x | | | |
| HR recovery | x | | | x | | |
| E90 | x | | | | | |
| BMI* | | x | x | | | |
| O2 pulse/VO2 slope | | | | | | |
| Circulatory Equivalent (Hanson) | | | x | | | |
| O2 desat | | | x | | x | |
| VO2 increase during recovery | | | x | | | |
| CRi slope | | | x | | | |
| Gxcap @ end exercise | | | | x | | |
| FEV1/FVC (Gold) | | | | | x | |
| IC rest - iC@end exercise (DH) | | | | | x | |
| FV1/FEV1 | | | | | | x |
| RR/VT slope | | | | | | x |
| Vtmax/Vtrest | | | | | | x |
| RR/VCO2 slope (Lung Stiffness) | | | | | | |
| (HR @ ESO-HR @ rest)/(Vepeak/MVV) | | | | | x | |
| HR@end exercise/MVV | | | | | x | |
| (PECO2/PecCO2)rest/(PECO2/PetCO2)@end exercise | | | | | | x |

Figure 11

| | Limits | | | Silo |
|---|---|---|---|---|
| | Low | Medium | High | |
| VE/VCO2 Slope | 30.0 | 36.0 | 45.0 | Heart |
| OUES | 1.5 | 1.2 | 1.1 | Heart |
| O2Pulse vs VO2 Slope | 3.5 | 3.0 | 1.8 | Heart |
| GxCap | 300.0 | 200.0 | 100.0 | Vascular |
| MPIpH Score | 0.0 | 2.0 | 4.0 | Vascular |
| Circulatory Equivalents | 90.0 | 80.0 | 60.0 | Heart |
| Desaturation (% absolute) | 5.0 | 7.0 | 10.0 | Obst Lung |
| FEV1 (Pct Pred) Rest LD | 70.0 | 60.0 | 50.0 | Rest Lung |
| FEV1/FVC % Obst LD | 80.0 | 50.0 | 30.0 | Obst Lung |
| Lung Stiffness (RR/VCO2 Slope) | 8.8 | 15.0 | 30.0 | Rest Lung |
| RR/VT Slope | 0.0 | 20.0 | 40.0 | Rest Lung |
| VT (Max Att/Resting) | 2.0 | 1.5 | 1.0 | Rest Lung |
| Dynamic Hyper Infl (L) | 0.5 | 0.0 | -0.2 | Obst Lung |
| VE(rer90)/MVV | 0.7 | 0.8 | 1.0 | Obst Lung |
| VO2/RR Slope | 5.0 | 6.0 | 7.0 | Deconditioned |
| HR Recovery | 30.0 | 20.0 | 15.0 | Deconditioned |
| VO2 Recovery | 0.0 | 7.0 | 10.0 | Heart |
| PECO2 Ratio | 0.9 | 0.8 | 0.6 | Rest AND Obs Lung |
| E100 males < 40 | 30.0 | 24.0 | 15.0 | Deconditioned |
| E100 Male 40-60 | 23.0 | 19.0 | 14.0 | Deconditioned |
| E100 Males > 60 | 16.0 | 14.0 | 10.0 | Deconditioned |
| E100 Females < 40 | 23.0 | 19.0 | 14.0 | Deconditioned |
| E100 Females 40-60 | 18.0 | 15.0 | 9.0 | Deconditioned |
| E100 Females > 40 | 13.0 | 11.0 | 6.0 | Deconditioned |
| E100 Obesity | 34.0 | 22.0 | 12.0 | Obesity |
| BMI Pct Ideal | 110.0 | 120.0 | 130.0 | Obesity |

PATTERN RECOGNITION SYSTEM FOR QUANTIFYING THE LIKELIHOOD OF THE CONTRIBUTION OF MULTIPLE POSSIBLE FORMS OF CHRONIC DISEASE TO PATIENT REPORTED DYSPNEA

RELATED APPLICATIONS

This application is a continuation of, and claims priority to, U.S. patent application Ser. No. 14/341,442, filed on Jul. 25, 2014, titled "PATTERN RECOGNITION SYSTEM FOR QUANTIFYING THE LIKELIHOOD OF THE CONTRIBUTION OF MULTIPLE POSSIBLE FORMS OF CHRONIC DISEASE TO PATIENT REPORTED DYSPNEA," which claims the benefit of U.S. Provisional Patent Application Ser. No. 61/858,140, filed Jul. 25, 2013 and the benefit of U.S. Provisional Patent Application Ser. No. 61/971,915, filed on Mar. 28, 2014; all of which are hereby incorporated by reference in their entireties.

TECHNICAL FIELD

The present disclosure relates generally to the field of medical diagnosis, including, but not limited to, diagnosing and quantifying diseases and conditions of the heart and lungs, including heart failure, pulmonary arterial hypertension, pulmonary venous hypertension, obstructed lung, restricted lung, obesity, and/or general deconditioning.

BACKGROUND

The early symptoms of chronic disease—such as dyspnea, dizziness, and fatigue—are often mild and are common to many other conditions. At rest, there are often no symptoms and no apparent signs of illness. As a result, detection of the cause of dyspnea and the severity of the dyspnea can be delayed for months or even years. Accordingly, the presence of one or more chronic diseases is frequently not recognized until the disease is relatively advanced. A specific chronic disease is often diagnosed only once other conditions have been investigated and ruled out.

The non-specific nature of symptoms associated with chronic disease means that the diagnosis cannot be made on symptoms alone. Using pulmonary hypertension (PH) as an example, a series of investigations is required to make an initial diagnosis, to refine that diagnosis in terms of clinical class of pulmonary hypertension, and to evaluate the degree of functional and hemodynamic impairment. Current PH evaluation and classification (type, functional capacity, hemodynamics) methods include blood tests and immunology, HIV test, abdominal ultrasound scan, 6-minute walk test (6-MWT), peak $VO_2$, right heart catheterization, and vaso-reactivity testing. It is with exercise in PH patients that the sympathetic and neuro-hormonal systems trigger increased vasoconstriction of the pulmonary arteriolar vascular beds, thus causing an elevation in pulmonary vascular resistance and reduced blood flow through the pulmonary vascular circuit. This response also increases the workload of the right heart during exercise. The reduced blood flow is mismatched to the air flow in the bronchioles and alveoli.

The World Health Organization (WHO) classifies pulmonary hypertension into distinct groups, including for example WHO Group 1 ("WHO 1"), WHO Group 2 ("WHO 2"), and WHO Group 3 ("WHO 3"), WHO Group 4 ("WHO 4"), and WHO Group 5 ("WHO 5"). Typically, the clinical differentiation of WHO 1 vs. WHO 2 or WHO 3 pulmonary hypertension, often termed primary vs. secondary PH, is confirmed by the invasive procedure of right heart catheterization (RHC) requiring the intravascular passage of a pressure monitoring catheter via the subclavian or cephalic vein into the right atrium, through the tricuspid valve and into the right ventricle with further maneuvering past the pulmonary valve and to the pulmonary artery (PA). The catheter is typically advanced further "downstream" in the PA with inflation of a distal tip balloon that occludes flow to allow for pressure monitoring of pressure on the pre-capillary side called a wedge pressure that has been reported to correlate well in most circumstance with left heart filling or left atrial pressures. The type of suspected pulmonary hypertension, whether true pulmonary arterial or venous hypertension is classified by hemodynamic criteria relative to the mean PA pressure and pulmonary wedge pressure values. The performing of a RHC imposes risk and often causes discomfort to the patient. Additionally, RHC is usually limited to gathering hemodynamic data while the patient is at rest without exertion due to the difficulties of supine patient exercise on the cath lab table.

SUMMARY

In general terms, this disclosure is directed to characterizing the contribution of chronic diseases or conditions to dyspnea in a patient. In one possible configuration and by non-limiting example, the contributions are characterized using spirometric and gas exchange data collected using a gas exchange test system. Various aspects are described in this disclosure, which include, but are not limited to, the following aspects. One aspect is a system for characterizing contributions of physiological conditions to dyspnea in a patient, the system comprising: a flow sensor configured to sense a respiratory flow of the patient; an analyzer configured to determine a composition of at least a portion of the respiratory flow of the patient; a computing device configured to: receive gas exchange measurements based on breath-by-breath data captured by the flow sensor and the analyzer during a gas exchange test; determine a first contribution value associated with a first physiological condition, wherein the first contribution value is based on the gas exchange measurements; determine a second contribution value associated with a second physiological condition, wherein the second contribution value is based on the gas exchange measurements; and output the first contribution value and the second contribution value.

Another aspect is a system for characterizing contributions of physiological conditions to dyspnea in a patient, the system comprising: a computing device configured to: receive gas exchange measurements based on breath-by-breath data captured by the flow sensor and analyzer during a gas exchange test; determine a first contribution value associated with a first physiological condition, wherein the first contribution value is based on the gas exchange measurements; determine a second contribution value associated with a second physiological condition, wherein the second contribution value is based on the gas exchange measurements; and output the first contribution value and the second contribution value.

Yet another aspect is a method for characterizing contributions of physiological conditions to dyspnea in a patient comprising: receiving results of a spirometry test on the patient, wherein the spirometry test includes a flow-volume loop; obtaining a plurality of spirometric measurements, including at least one of forced vital capacity (FVC), inspiratory capacity (IC), and forced expiratory volume in one second (FEV1); performing, using a cardiopulmonary exercise gas exchange analyzer, a gas exchange test on the patient, wherein the gas exchange test includes a rest phase, an exercise phase, and a recovery period, wherein the patient performs exercise during the exercise phase; obtaining a plurality of gas exchange measurements, including end tidal $CO_2$, on a breath-by-breath basis during the gas exchange test; determining a first contribution value associated with a first physiological condition, wherein the first contribution value is based on at least one of the plurality of spirometric measurements and at least one of the plurality of gas exchange measurements; determining a second contribution value associated with a second physiological condition, wherein the second contribution value is based on at least one of the plurality of gas exchange measurements; and displaying the first contribution value and the second contribution value.

A method for characterizing contributions of physiological conditions to dyspnea in a patient comprising: performing a spirometry test on the patient using a flow sensor of a cardiopulmonary exercise gas exchange analyzer, wherein the spirometry test includes a flow-volume loop; obtaining a plurality of spirometric measurements, including force vital capacity (FVC), inspiratory capacity (IC), and forced expiratory volume in one second (FEV1); performing, using the cardiopulmonary exercise gas exchange analyzer, a gas exchange test on the patient, wherein the gas exchange test includes a rest phase, an exercise phase, and a recovery period, wherein the patient performs exercise during the exercise phase; obtaining a plurality of gas exchange measurements, including end tidal $CO_2$, on a breath-by-breath basis during the gas exchange test; determining a first contribution value associated with a first physiological condition, wherein the first contribution value is based on at least one of the associated with a first weighted combination of at least one of the plurality of spirometric measurements and at least one of the plurality of gas exchange measurements; determining a second contribution value associated with a second physiological condition, wherein the second contribution value is associated with a second weighted combination of one or more of the plurality of spirometric measurements and at least one or more of the plurality of gas exchange measurements; retrieving historical test data relating to a previous gas exchange test on the patient; generating a user interface that includes a first visual indicator, a second visual indicator, a third visual indicator, and a fourth visual indicator, wherein a property of the first visual indicator is determined based on the first contribution value, a property of the second visual indicator is determined based on the second contribution value, a property of the third visual indicator is determined based on a first historical contribution value associated with the first physiological condition and being based on the historical test data, and a property of the fourth visual indicator is determined based on a second historical contribution value associated with the second physiological condition and being based on the historical test data.

Yet another aspect is a method for classifying pulmonary arterial hypertension (PAH) in a patient: performing, using a cardiopulmonary exercise gas exchange analyzer, a gas exchange test on the patient, wherein the gas exchange test includes a rest phase, an exercise phase, and a recovery period, wherein the patient performs exercise during the exercise phase; obtaining a plurality of physiological measurements, including end tidal $CO_2$, on a breath-by-breath basis during the gas exchange test; determining a heart failure functional status of the patient based on at least some of the plurality of physiological measurements; determining a pulmonary hypertension functional status of the patient based on at least some of the plurality of physiological measurements; classifying the pulmonary hypertension based on the pulmonary hypertension functional status and the heart failure functional status.

BRIEF DESCRIPTION OF THE DRAWINGS

FIG. 2 is an example embodiment of a database table 150 for storing data acquired by the gas exchange testing system of FIG. 1.

FIG. 10 is an example table that is used in some embodiments of the gas exchange testing system of FIG. 1 to associate various physiological values with silos.

FIG. 11 illustrates an example table that is used in some embodiments of the gas exchange testing system of FIG. 1 to calculate silo scores for various physiological values.

DETAILED DESCRIPTION

Figure 1:
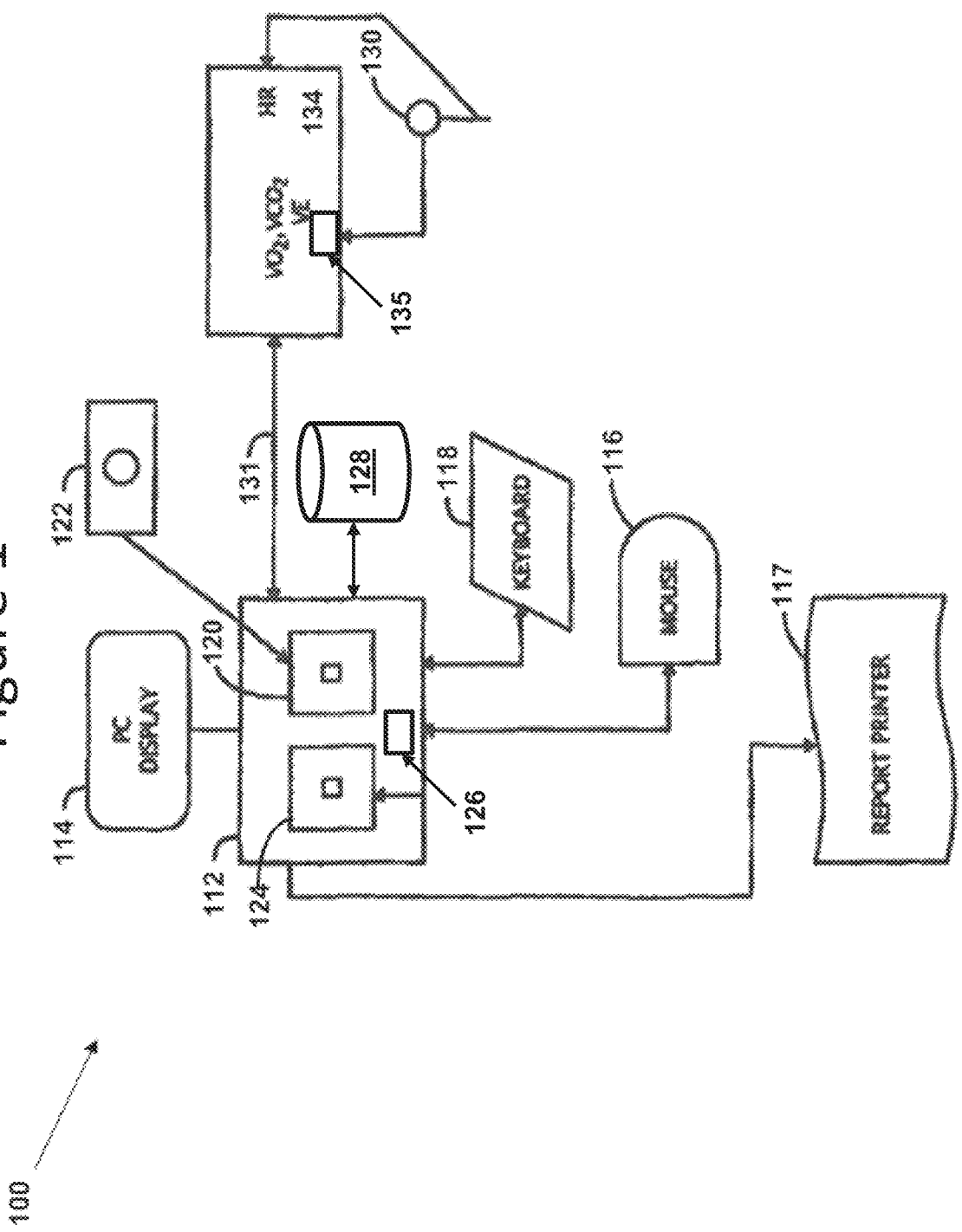
FIG. 1 illustrates an embodiment of a gas exchange testing system 100.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

There exists a clinical need to determine the most likely causes of dyspnea during mild to moderate exercise and to make clinically available a more accurate means of directing physician referral for additional standard of care tests. The current clinical pathways are inefficient in that referrals are frequently made to the wrong specialist. Some embodiments of the present disclosure are intended to streamline therapy and enhance the success for disease treatment by more accurately predicting the likelihood of a primary disease and suggesting which other diseases may be a secondary cause of the dyspnea.

In general, the present disclosure describes systems and methods for quantifying and differentiating chronic diseases contributing to dyspnea in a patient. In at least some embodiments, physiological measurements are obtained from the patient during a gas-exchange test and a spirometry test. Further, in at least some embodiments, physiological values are calculated based on one or more of the physiological measurements. In at least some embodiments, a score corresponding to the likelihood that a particular chronic disease is contributing to dyspnea is calculated based on the physiological measurements or physiological values. This score is an example of a contribution value. In at least some embodiments, a chart that represents the scores corresponding to the likelihood that particular chronic diseases are contributing to dyspnea is displayed. In some embodiments, some or all of the chronic diseases are represented as a vertical disease silos, each having a height corresponding to the likelihood that the associated chronic disease is contributing to dyspnea.

At least some embodiments of the systems and methods disclosed are more sensitive, physiologic, and easier to use than currently available disease differentiation methods. In addition, in at least some embodiments, feedback is provided during long-term follow-up and treatment in patients with chronic diseases.

In at least some embodiments, a global assessment of multiple chronic diseases and their effect on causing dyspnea in a patient is provided. Additionally, in at least some embodiments, differentiation between chronic diseases and sub-types of chronic diseases are provided. These benefits are not available with indexes or classification systems that are focused on a single disease.

Typically, in the clinical setting, resting spirometry is performed separately from cardiopulmonary exercise testing with breath-by-breath gas exchange monitoring. It is known that resting spirometry data may not by itself predict functional exercise limitations. It is often that the exercise state is not evaluated by any pulmonary function parameters that truly represent gas exchange in the lungs. Instead, walking distance and peak oxygen uptake are measured.

In at least some embodiments, the spirometric data is collected during the same clinic office visit as the exercise gas exchange test using the same flow transducer and patient preparation, thereby reducing the clinical diagnostic time. In at least some embodiments, the spirometric data includes key measures of the patient's flow volume loop (FVL), including forced vital capacity (FVC), forced expiratory volume in one second (FEV1), and inspiratory capacity (IC). In some embodiments the ratio of FEV1 to FVC is calculated and used as a determinant of the existence of Chronic Obstructive Pulmonary Disease (COPD) as a disease silo, in addition to inspiratory capacity (IC) for supportive evaluation of potential restrictive patterns of lung disease.

The Gold Criteria, which uses the measured values for FVC and FEV1, is used for determining whether a patient has restrictive or obstructive lung disease. The Gold Criteria, when applied to restrictive LD, produces a number between 0 and 3 in the restrictive LD silo. When applied to obstructive LD, the Gold Criteria produces a number between 0 and 3 in the obstructive LD silo.

The existence of COPD can offer an explanation of potential hyperinflation during exercise observed with other select gas exchange variable patterns. The performance of an FVL by the patient prior to collecting resting, exercise, and recovery data is intended to provide multivariable descriptors of different potential chronic disease silos to aid in the most accurate evaluation of the likely cause of exertional dyspnea. The data obtained from the FVL can offer an explanation of the cause of a reduction in oxygen uptake in the lungs.

The determination of key pulmonary variables by the FVL measurement also aids in the differentiation of different classes of pulmonary hypertension as well as the determination of existing co-morbidities that together worsen the systems of exertional dyspnea. The use of the FVL can also help guide the correct path for patient therapy, upon determining the likely cause or causes of dyspnea.

Additionally, in at least some embodiments, data collected during the exertional state of a gas exchange test is used to detect the existence of PH before it has advanced to a state where its symptoms are present during rest. This may beneficially allow detection and diagnosis of PH at an early stage. If PH is detected later, treatment becomes more challenging and the pulmonary vascular bed becomes more stiff and conducive to elevated PA pressure. In addition, earlier detection of PH may minimize or delay the chronic vascular damage and eventual failure caused by right ventricular strain associated with PH.

Additionally, in some embodiments, multiple chronic disease indexes are used to differentiate between sub-types of a particular chronic disease. For example, in some embodiments, the gas exchange testing system 100 differentiates WHO 1 pulmonary hypertension from WHO 2 and 3 pulmonary hypertension based on separate indexes for heart failure and pulmonary hypertension. The MultiVariable Index (MVI) described in U.S. Pat. No. 8,630,811, titled METHOD FOR COMBINING INDIVIDUAL RISK VARIABLES DERIVED FROM CARDIOPULMONARY EXERCISE TESTING INTO A SINGLE VARIABLE and issued on Jan. 14, 2014, is an example of an index associated with heart failure. The MultiParametric Index for Pulmonary Hypertension (MPIph) described in U.S. patent application Ser. No. 12/567,005, titled PATTERN RECOGNITION SYSTEM FOR CLASSIFYING THE FUNCTIONAL STATUS OF PATIENTS WITH PULMONARY HYPERTENSION, INCLUDING PULMONARY ARTERIAL AND PULMONARY VASCULAR HYPERTENSION and filed on Sep. 25, 2009 is an example of an index associated with pulmonary hypertension. In some embodiments, MVI and MPIph or associated values are used to differentiate between sub-types of pulmonary hypertension.

In accordance with the present disclosure, a new and novel method, Disease Risk and Referral optimization (DR2), is disclosed for determining the relative likelihood of the presence of one or more chronic diseases. In addition, in at least some embodiments, DR2 makes it easier for a wide variety of physicians to visualize and interpret combined pulmonary function and cardiopulmonary exercise tests.

Moreover, in at least some embodiments, data to implement this method is obtained at rest and during exercise—either maximally or submaximally.

In at least some embodiments, a cardiopulmonary exercise gas exchange system is configured to perform a Flow/Volume loop as well as to measure gas exchange variables during rest, exercise, and recovery. In some embodiments, the measurements are captured using the SHAPE HF™ Cardiopulmonary Exercise Testing System, available from Shape Medical Systems, Inc. of St. Paul, Minn. Other embodiments include other systems to capture the measurements. In at least some embodiments, the feature extraction engine and the classification engine enable an observer to gain new and valuable insight into the present condition and condition trends in patients.

Referring now to FIG. 1, an embodiment of a gas exchange testing system 100 is shown. The gas exchange testing system 100 includes a computing device 112, a gas exchange measurement device 134, and a database 128. Also shown is a patient or subject 130.

In some embodiments, the computing device 112 includes a display terminal 114 with an associated mouse 116, report printer 117, and keyboard 118. The mouse 116 and the keyboard 118 are examples of user input devices. Some embodiments include additional or different user input devices such as a touch-sensitive display screen or a voice recognition system. The system further includes a storage handler 120 with an associated computer-readable memory storage device 122. The computer-readable memory storage device 122 is an example of a computer-readable data storage device. As is well known in the art, the storage handler 120 input/output interfaces comprise read/write devices for reading, deleting, adding, or changing information stored on a machine-readable medium, e.g., a thumb drive, and for providing signals which can be considered as data or operands to be manipulated in accordance with a software program loaded into the memory 126. Examples of the memory 126 include RAM or ROM. In some embodiments, the memory storage device 122 includes non-transitory storage devices. The computing device also includes a processor 124.

In some embodiments, the gas exchange test is a cardiopulmonary exercise test. In these embodiments, the exercise protocol includes exercise equipment (not shown), such as a bicycle ergometer, stair step, or treadmill. The subject 130 uses the exercise equipment during a portion of the test. The gas exchange measurement device 134 includes a flow sensor 135 configured to sense a respiratory flow of the patient and can determine components of the respiratory flow of the patient, including the concentration of oxygen and carbon dioxide in the respiratory flow. During the gas exchange test, the gas exchange measurement device 134 may also measure various physiological parameters associated with the subject. In some embodiments, these physiological parameters include heart rate (HR), respiratory rate (RR), ventilation (VE), rate of oxygen uptake or consumption ($VO_2$), carbon dioxide production ($VCO_2$), and oxygen saturation ($SaO_2$). In other embodiments, other physiological parameters are measured as well. In addition, in some embodiments, the physiological parameters include also include forced vital capacity (FVC), forced expiratory volume in one second (FEV1), and inspiratory capacity (IC). The gas exchange measurement device 134 is an example of an analyzer. In addition, the gas exchange measurement device 134 is also an example of a spirometer.

In some embodiments, the physiological data that is measured by the gas exchange measurement device 134 is transmitted to the computing device 112 via a conductor 131, such as a cable. In other embodiments, the physiological data is transmitted to the computing device wirelessly. In other embodiments, other communication devices are used to transmit the physiological data to the computing device 112. In some embodiments, the display terminal 114 displays the physiological data or other values derived from the physiological data.

The computing device 112 may comprise a personal computer, a dedicated microcontroller configured to acquire the measurements and process those measurements, a mobile computing device, such as a smart phone or tablet, or a server computer. Therefore, the further detailed description will be made independent of the type and characteristics of the computing device 112.

The database 128 stores data in an organized manner, such as in a hierarchical or relational database structure, or in lists and other data structures such as tables. Although the database 128 is illustrated as being separated from the computing device 112, in some embodiments the database 128 is located on the computing device 112. In some embodiments, the data acquired by the gas exchange testing system 100 is stored in the database 128 in one or more relational database tables.

An example of one embodiment of a relational database table 150 for storing data acquired by the gas exchange testing system 100 is illustrated in FIG. 2. The table 150 contains a plurality of rows 152, each of which represents data captured during a breath of the gas exchange test. Each of the rows 152 includes a key 154, a test key 156, a phase 158, and measurement data 160.

The key 154 is used by other tables in the database to reference a particular breath/row. The test key 156 is a foreign key to a test table (not shown) in the database 128. Using the test key 156, each breath/row is associated with a test. The phase 158 associates the breaths/rows of data for each patient and each test, including data associated with the flow/volume loop, with the appropriate phase (e.g., rest, exercise, or recovery) for use in feature extraction and classification.

Additionally, the table 150 includes multiple columns of measurement data 160. In the example shown, the measurement data includes a breath count, $PetCO_2$, $VCO_2$, $VO_2$, VT, Heart Rate, Respiratory Rate, and Barometric Pressure. In other embodiments, more, fewer, or different measurements are stored in each row.

Figure 3:
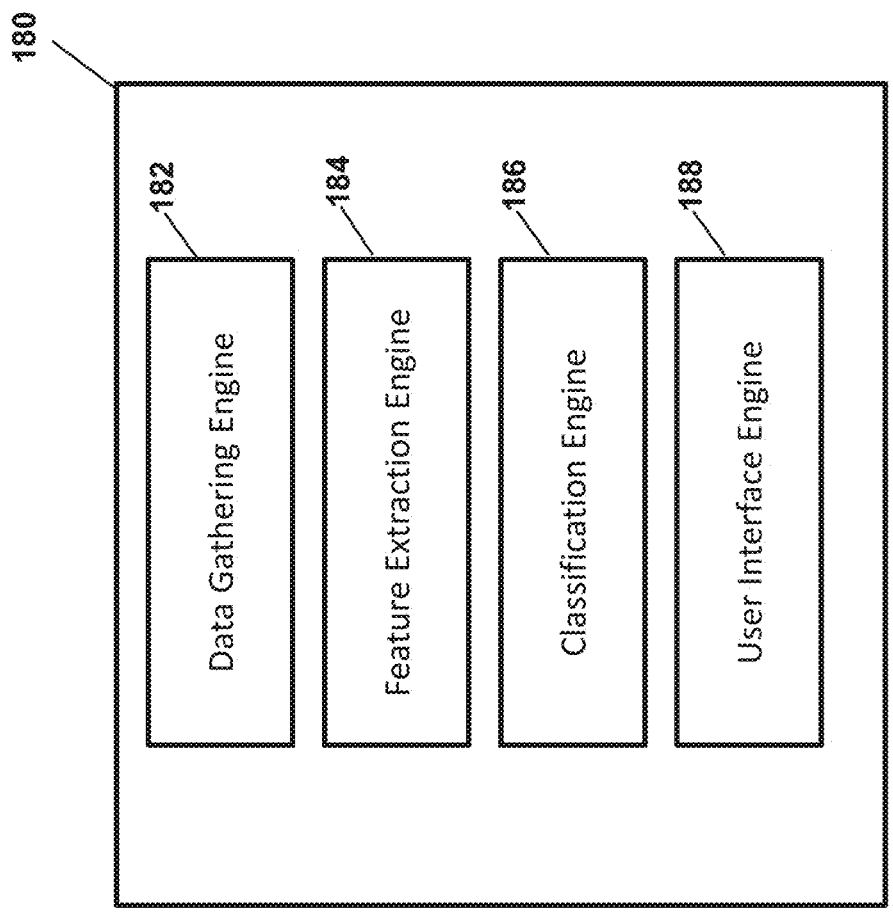
FIG. 3 illustrates a schematic diagram of an embodiment of a pattern recognition system of some embodiments of the gas exchange testing system of FIG. 1.

FIG. 3 illustrates a schematic diagram of an embodiment of a pattern recognition system 180 that is included in some embodiments of the gas exchange testing system 100. The pattern recognition system 180 includes a data gathering engine 182, a feature extraction engine 184, a classification engine 186, and a user interface engine 188.

The data gathering engine 182 operates to receive physiological measurements and other observations from the gas exchange measurement device 134. In some embodiments, the data gathering engine 182 receives measurements or observations from other sources as well. As an example, FVC, FEV1, and IC could be measured on a separate spirometer, manually entered, and stored in the database 128. Similarly, the presence or absence of periodic breathing could be determined by physician observation, manually entered, and stored in the database 128. In some embodiments, the data gathering engine 182 processes the measurements and observations and stores them in the database 128. The feature extraction engine 184 operates to compute numeric information from the measurements and observations. The classification engine 186 operates to classify or describe the measurements or observations based on the extracted features. The user interface engine 188 operates to generate a user interface to convey information to and receive information from a user.

Figure 4:
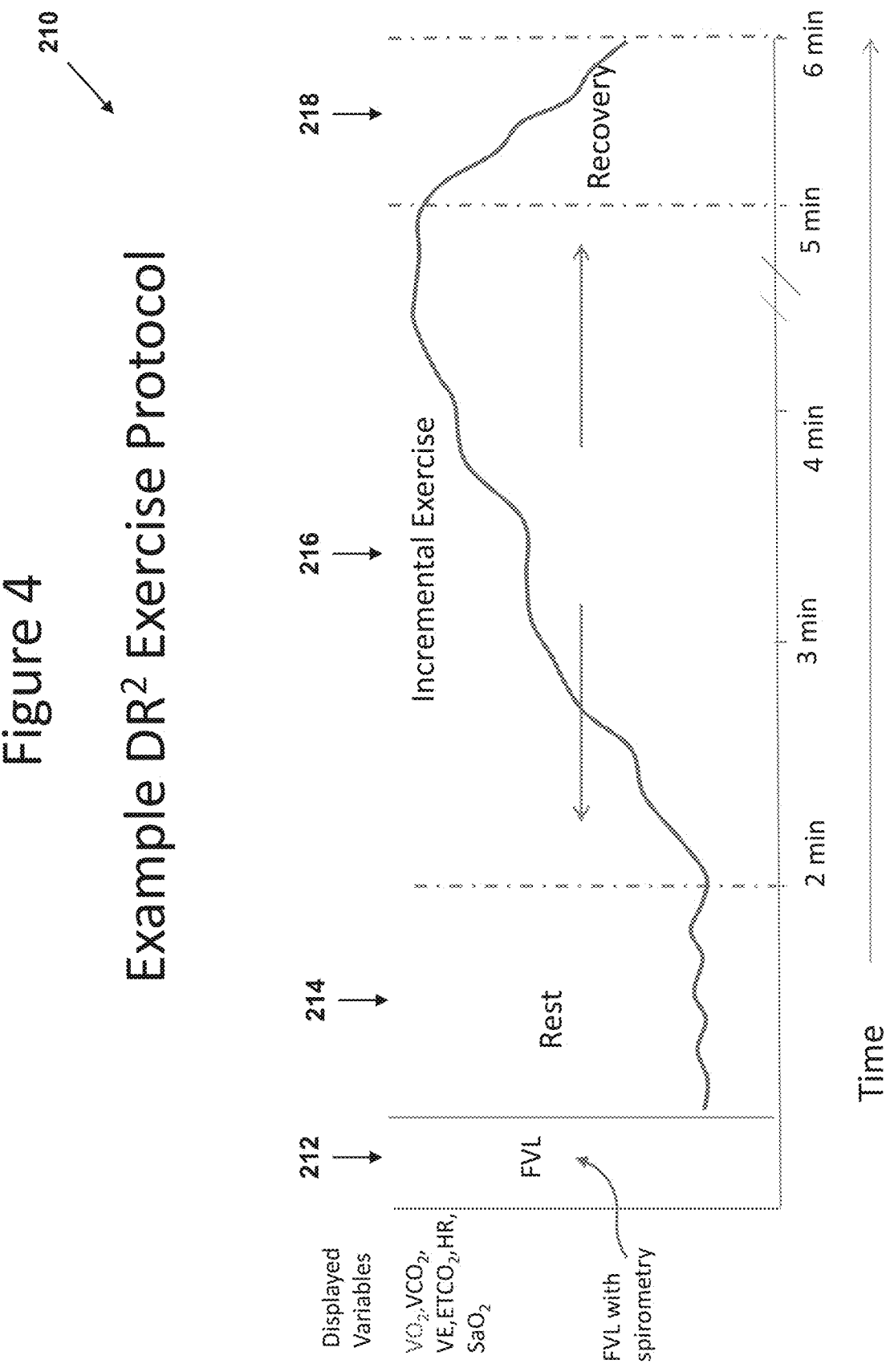
FIG. 4 illustrates an example test protocol for use with some embodiments of the gas exchange testing system of FIG. 1.

FIG. 4 illustrates an example test protocol 210 for determining the likely cause or causes of dyspnea for use with some embodiments of the gas exchange testing system 100. The test protocol includes an FVL phase 212, a rest phase 214, an incremental exercise phase 216, and a recovery phase 218. In some embodiments, the data gathering engine 182 captures data during one or more of these phases and the feature extraction engine 184 and the classification engine 186 process the data to classify the functional status of patients with dyspnea and to identify the likelihood of the primary and secondary causes of dyspnea.

In the protocol 210, the FVL phase 212 is performed first. During the FVL phase 212, the patient performs an FVL spirometry test.

Figure 5:
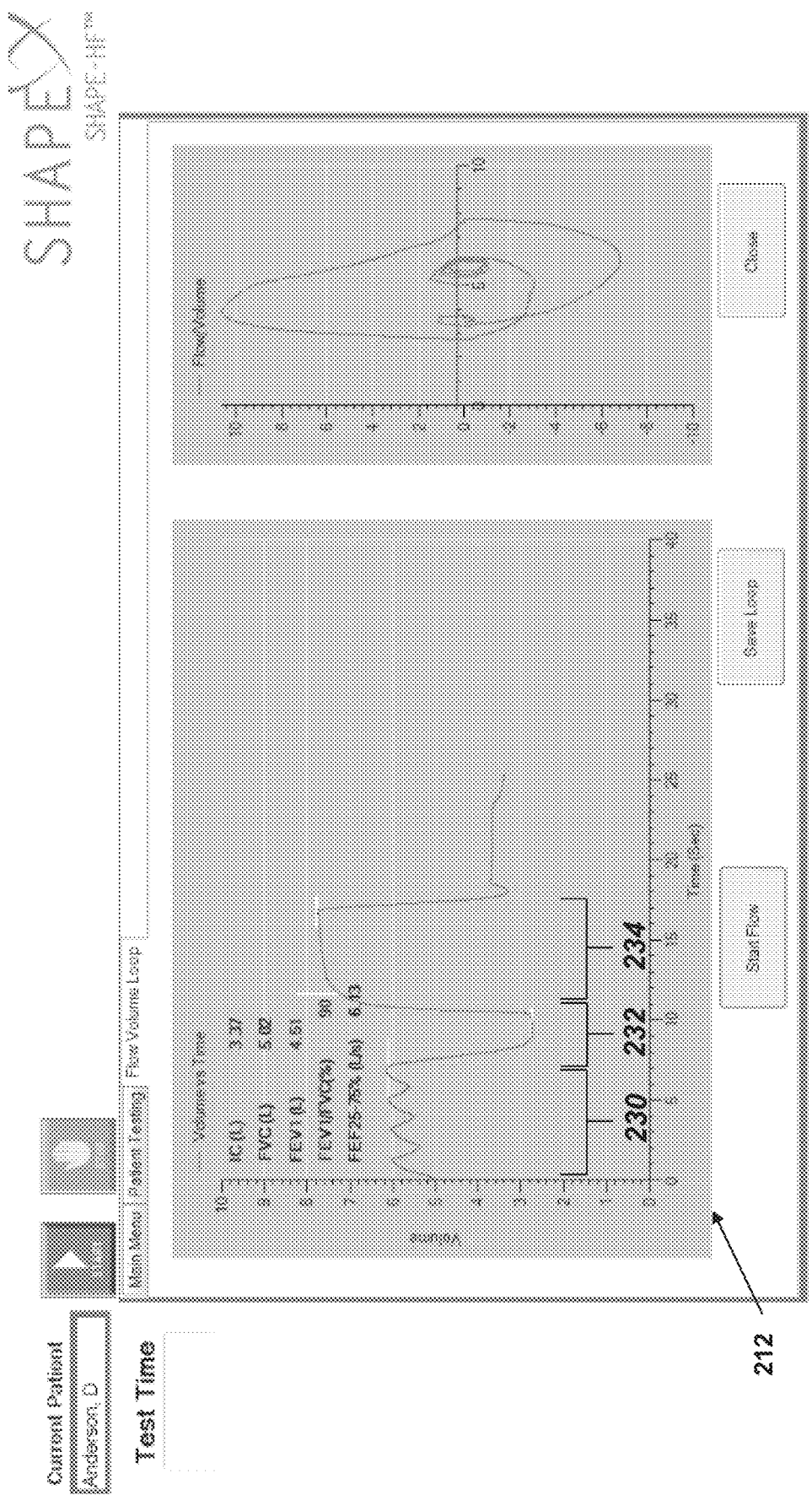
FIG. 5 illustrates the flow volume loop (FVL) phase of the test protocol of FIG. 4.

FIG. 5 illustrates the FVL phase and shows example data gathered during the FVL phase 212. During operation 230 of the FVL phase 212, the patient is asked to breath slowly into the system pneumotach while seated until a stable breathing pattern is observed. Next, at operation 232, the patient breathes in as deeply as possible. Next, at operation 234, the patient blows out as hard and as long as possible. The patient is then asked to breathe normally again.

Returning to FIG. 4, the FVL phase 212 is followed by the rest phase 214. During the rest phase 214, gas exchange measurements are collected by the data gathering engine 182 while the patient rests. In some embodiments, the gas exchange measurements are used for determination of Periodic Breathing (PB), Heart Rate variability (HRV), and/or breathing frequency characterized by Poincare plots and/or electrocardiograph ST segment analysis. In other embodiments, the gas exchange measurements are used for other purposes as well. Although shown as lasting two minutes, in some embodiments the rest phase 214 lasts for a longer or shorter time.

During the exercise phase 216, the patient performs submaximal or maximal exercise while gas exchange measurements are captured by the data gathering engine 182. In some embodiments, the patient incrementally increases the intensity of exercise throughout the exercise phase 216. In some embodiments, the exercise phase 216 has a fixed duration. Although shown as lasting three minutes, in some embodiments the exercise phase 216 lasts for a longer or shorter time.

Additionally, in some embodiments, the exercise phase continues until the patient achieves a predetermined target metric. For example, in some embodiments, the target metric is a heart rate equal to or greater than 60-90% of the age predicted max heart rate. In other embodiments, the target metric is a respiratory exchange rate (RER) greater than or equal to 0.90. In other embodiments, other target metrics are used as well. In some embodiments, the gas exchange testing system 100 indicates (e.g., audibly or visually) that the predetermined target metric is achieved.

During the recovery phase 218, the patient rests again while the data gathering engine 182 collects gas exchange measurements. In some embodiments, the gas exchange measurements captured during the recovery phase 218 are used to determine heart rate and oxygen consumption (VO2) recovery values. In other embodiments, the gas exchange measurements captured during the recovery phase 218 are used for other purposes as well. Although shown as lasting for one minute, in some embodiments, the recovery phase 218 lasts for a longer or shorter time.

The protocol 210 is merely an example. In other embodiments, other protocols are used that include fewer, more, or different phases. Additionally, in some embodiments, the FVL phase 212 is combined with the rest phase 214. Other embodiments are possible as well.

In some embodiments, the general class of data utilized is cardiopulmonary exercise gas exchange measurements obtained 1) at rest, 2) during physical exercise testing performed in accordance with a standardized workload protocol as the forcing function to elicit physiologic changes resulting from the workload, and 3) during a short recovery period following exercise termination. The data measured during exercise quantifies how an individual is able to function in the physical world in terms of the physiologic changes that the individual experiences when engaged in the performance of daily physical work.

In addition, in some embodiments, a flow/volume loop is performed prior to the start of the collection of gas exchange measurements. The measurements indicated in FIG. 4 are made using the same pneumotach used by the CPX using software that collects continuously transmitted samples of respiratory flow as measured by the system differential pressure transducer at the rate of 200 samples/second.

In some embodiments, the physiologic changes that result from an increased exercise load are measured using a CPX system to measure selected variables associated with oxygen consumption ($VO_2$), carbon dioxide production ($VCO_2$), end tidal $CO_2$ ($ETCO_2$), ventilation (VE), heart rate (HR), and oxygen saturation ($SaO_2$). In other embodiments, more, fewer, or different variables are captured as well.

Figure 17:
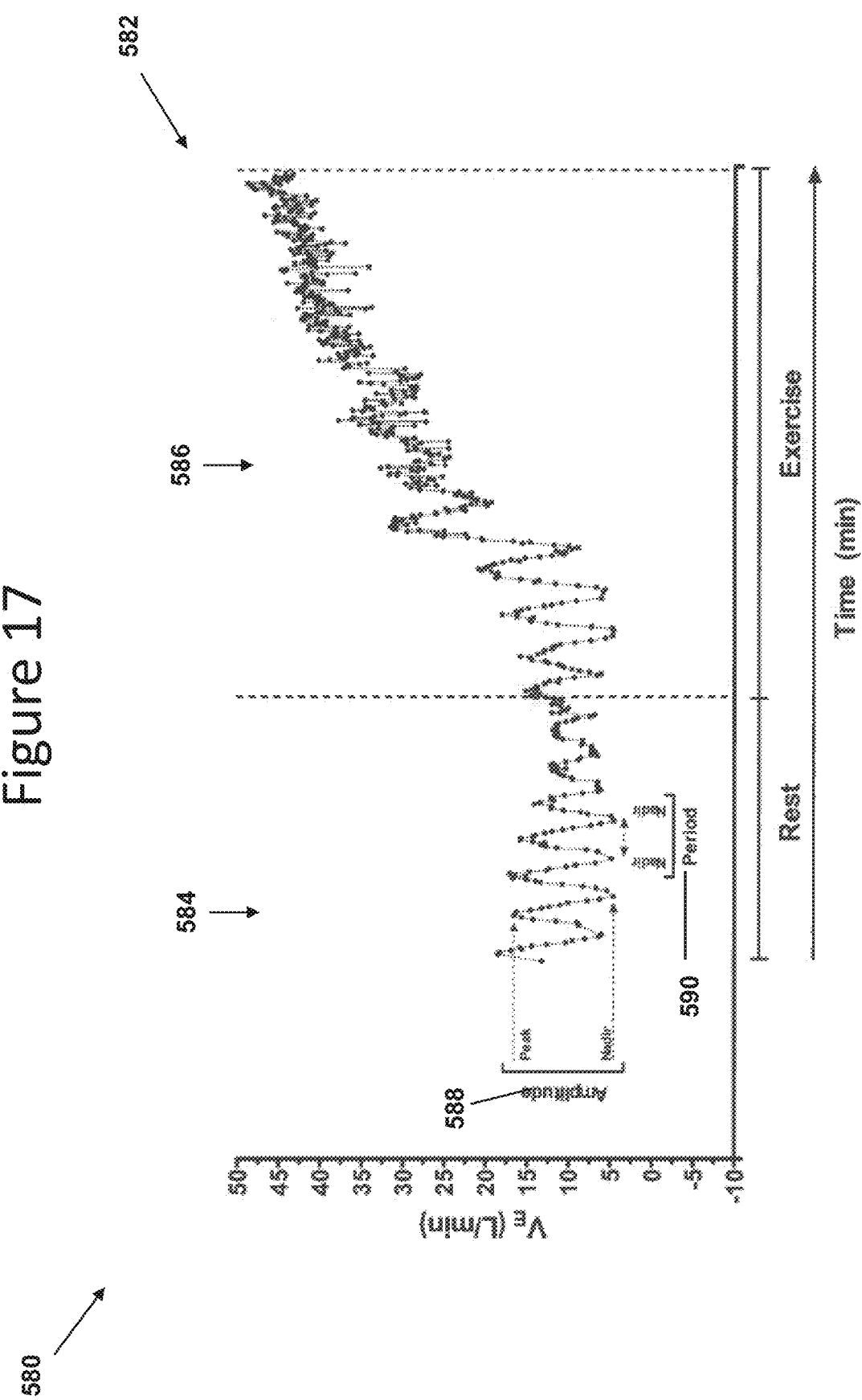
FIG. 17 illustrates a graph of breath data captured by some embodiments of the gas exchange testing system of FIG. 1.

Additionally, in at least some embodiments, one or more of resting data and exercise data are analyzed to determine some or all of the following additional variables:

Periodic Breathing (PB): Periodic breathing and exercise-induced oscillatory ventilation refer to a regular cycle of increasing and decreasing ventilation during rest or exercise respectively. In some embodiments, periodic breathing is represented as binary variable, indicating whether periodic breathing was observed. In some embodiments, this variable is set by a physician through the user interface of the system. In other embodiments, this variable is quantified using computer software in terms of analysis of the amplitude and period of oscillation measured. For example, at least some embodiments use one or more of peak detection algorithms, sine wave fitting algorithms, and Fourier analysis to identify periodic breathing. FIG. 17 illustrates a graph 580 of breath data 582 captured by some embodiments of the gas exchange testing system 100. The breath data 582 includes a plurality of points representing individual breaths captured during a rest phase 584 and an exercise phase 586 of a patient test. Each point representing a breath is plotted at location in the graph 580 corresponding to VE (in liters/minute) of the breath and the time during the test the breath occurred. This example graph illustrates periodic breathing during the rest phase 584 and at the beginning of the exercise phase 586. The amplitude 588 and period 590 of the periodic breathing is also shown.

Heart Rate Variability (HRV): In some embodiment, heart rate variability is represented as a numeric value corresponding to the variation in the time interval between heartbeats. It is measured by the variation in the beat-to-beat interval as recorded by the DR2 system electrocardiogram.

Figure 16:
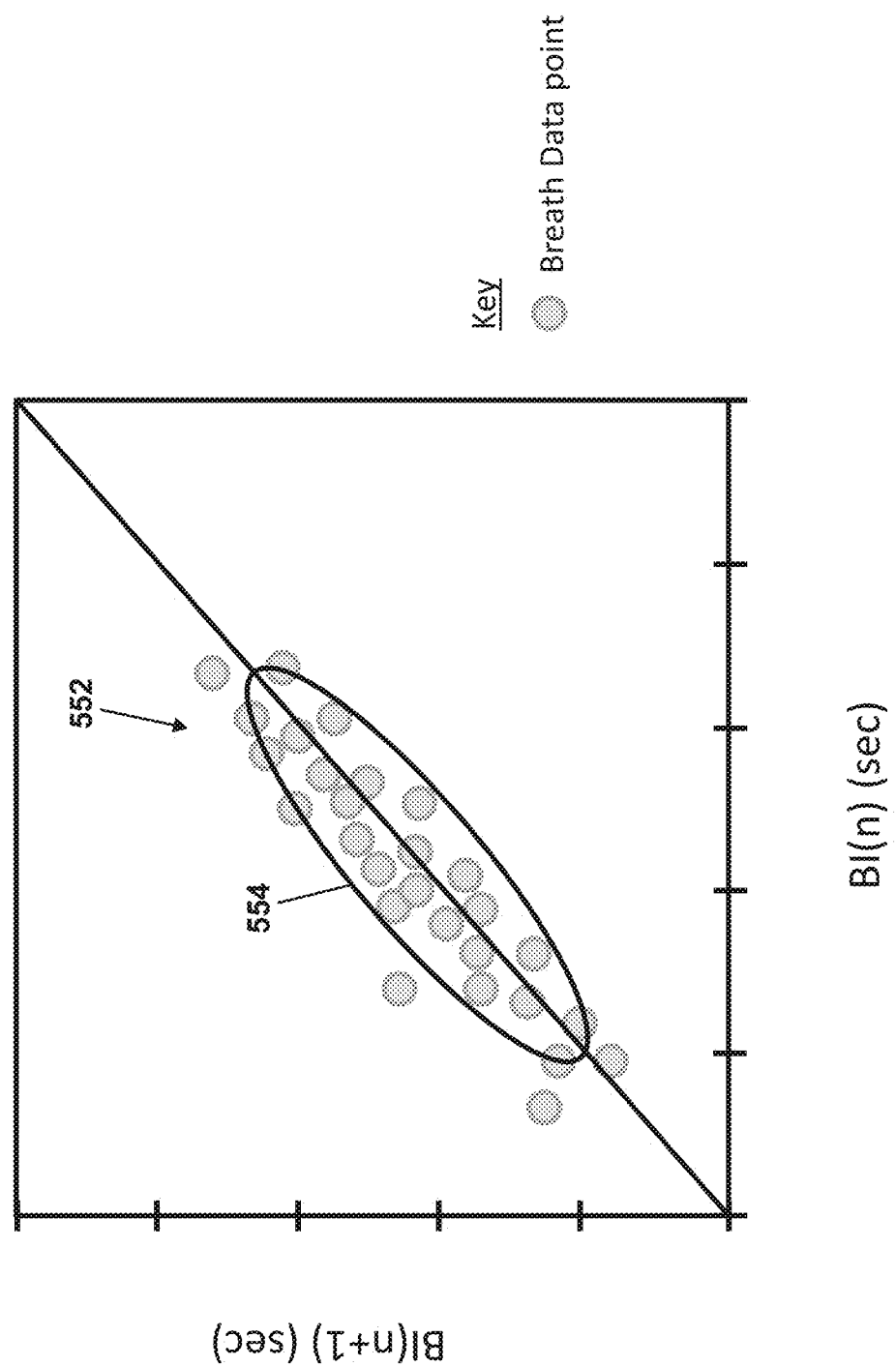
FIG. 16 illustrates a Poincare plot of breath data from some embodiments of the gas exchange testing system of FIG. 1.

Respiratory Rate Variability (RRV): In some embodiments, breathing frequency is plotted in a Poincare plot or return map to quantify self-similarity in the periodic breath functions. In some embodiments, the breathing interval for each breath, BI(n), is plotted against the breathing interval for the breath that follows it, BI(n+1). The breathing interval is defined as expiratory time plus inspiratory time. FIG. 16 illustrates a Poincare plot 550 of breath data from some embodiments of the gas exchange testing system 100. In the example shown in FIG. 16, a series of breaths 552 are plotted. BI(n) is plotted on the x-axis, while BI(n+1) is plotted on the y-axis. In some embodiments, the shape of this plot is analyzed to determine whether variability in respiratory rate or breathing frequency is present. In at least some embodiments, the plot is displayed on a display device and a user enters a value indicating the presence or absence of respiratory rate variability through the user interface. In other embodiments, the presence, absence, or magnitude of respiratory rate variability is determined using computer software. For example, in at least some embodiments, an ellipse 554 is fit to the breaths 552 using ellipse fitting techniques. In some embodiments, properties of the ellipse 554, such as eccentricity are used to identify and quantify respiratory rate variability. In at least some embodiments, one of the purposes of such a display is to determine patient activity and/or inefficiency of breathing work relative to the patient's disease status. Such data may provide non-invasive insight as to the accumulation of fluid in the HF patient with acute decompensation.

ST Segment Analysis: In at least some embodiments, the detection of coronary artery disease, as a subset of the heart disease silo, can be identified as the possible cause of dyspnea. In some embodiments, simultaneous monitoring of a 12 channel electrocardiograph (ECG) can provide real-time evidence of electrocardiographic changes indicative of ischemia, as indicated by significant ST depression of 2 mm or greater in one or multiple precordial or limb leads. In combination with alterations in gas exchange measurements, ischemia detection would be enhanced with the addition of select parameters such as (1) a significant downward slope shift in the O2P profile pattern, relative to increasing VO2 or work, (2) a low ventilatory threshold point less than 40% predicted, (3) a decrease in the ETCO2 profile (4) flattening or attenuation of the pulmonary capacitance pattern and (5) a rise in the V/Q ratio. In some embodiments, a real time plot of the ST segment changes with select gas exchange variable would assist in the alignment of ischemia onset with functional cardiopulmonary changes in order to mark the onset of left ventricular dysfunction due to the mismatching of blood flow demands of the heart with coronary perfusion.

In some embodiments, some or all of the data captured during the protocol 210 is stored in the database 128.

Figure 6:
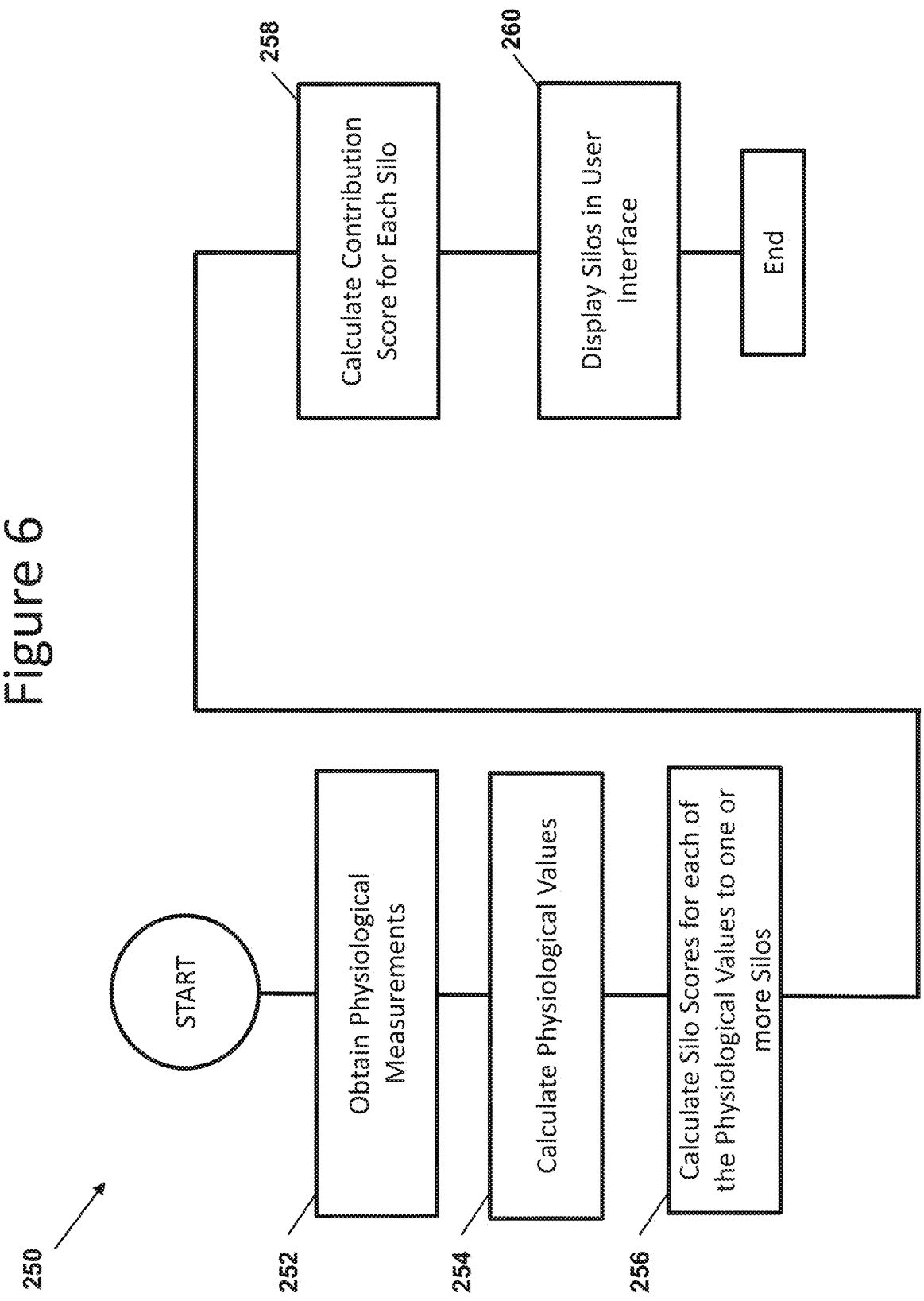
FIG. 6 is a flow chart illustrating an example method of operating the feature extraction engine and the classification engine of FIG. 3.

FIG. 6 is a flow chart illustrating an example method 250 of operating the feature extraction engine 184 and the classification engine 186. In this example, the method 250 includes operations 252, 254, 256, 258, and 266.

At operation 252, physiological measurements are obtained. In some embodiments, the physiologic measurements are obtained from the database 128. In other embodiments, the physiological measurements are obtained directly from the data gathering engine 182. Yet other embodiments are possible as well.

At operation 254, physiological values are calculated based on the physiological measurements. In some embodiments, the physiological values are based on one or more of the physiological measurements. Additionally, in some embodiments, at least some of the physiological values are calculated based on values that are entered into the user interface by a user. Examples of the physiological values that are calculated in some embodiments are illustrated and described in greater detail with respect to FIG. 10.

At operation 256, silo scores are calculated for each of the physiological values relating to one or more silos. In some embodiments, silos are predefined in terms of specific disease classes or conditions. For example, in some embodiments, silos are predefined for one or more of Deconditioned, Obesity, Heart Disease, Pulmonary Vascular or Pulmonary Arterial Hypertension and Pulmonary Venous Hypertension, Obstructive Lung Disease, and Restrictive Lung Disease. Each silo is associated with a specific set of calculated physiological values calculated in operation 254. For each of the silos, the associated physiological values are evaluated to calculate a silo score for that physiological value. For example, in some embodiments, a silo score from 0 to 3 is calculated for each physiological value, where 0 represents none, 1 represents slight, 2 represents moderate, and 3 represents strong. In some embodiments, the silo scores are calculated by comparing the calculated physiological value to predetermined thresholds. Examples of some embodiments of the predetermined threshold values are illustrated and described in greater detail with respect to FIG. 11.

At operation 258, a contribution score is calculated for each of the silos. In some embodiments, the contribution score indicates the likelihood that the disease or condition associated with the silo contributes to the dyspnea. In some embodiments, the contribution score for a silo is calculated by averaging the silo scores for all of the physiological values associated with the silo. In some embodiments, the contribution score is based on a weighted average of the silo scores of the associated physiological values. In some embodiments, the silo scores are weighted equally. In some embodiments, the contribution value for each silo represents the strength of the evidence that the particular disease or condition is suspected. In some embodiments, the contribution value for each silo is a numeric value from 0 to 3, where 0 represents none, 1 represents slight, 2 represents moderate, and 3 represents strong.

At operation 260, the silos are displayed on the user interface. In some embodiments, the silos are displayed as vertical columns, where the height of the column is associated with the contribution score for the silo. An example embodiment of a user interface for displaying disease silos is illustrated and described in greater detail with respect to FIG. 8. In some embodiments, the user interface also includes a pop-up information button associated with each of the silos that when clicked will display a pop-up information window of the measured values and scores of each of the constituent physiological values of the silo. An example embodiment of the pop-up information window is illustrated and described in greater detail with respect to FIG. 9.

Figure 7:
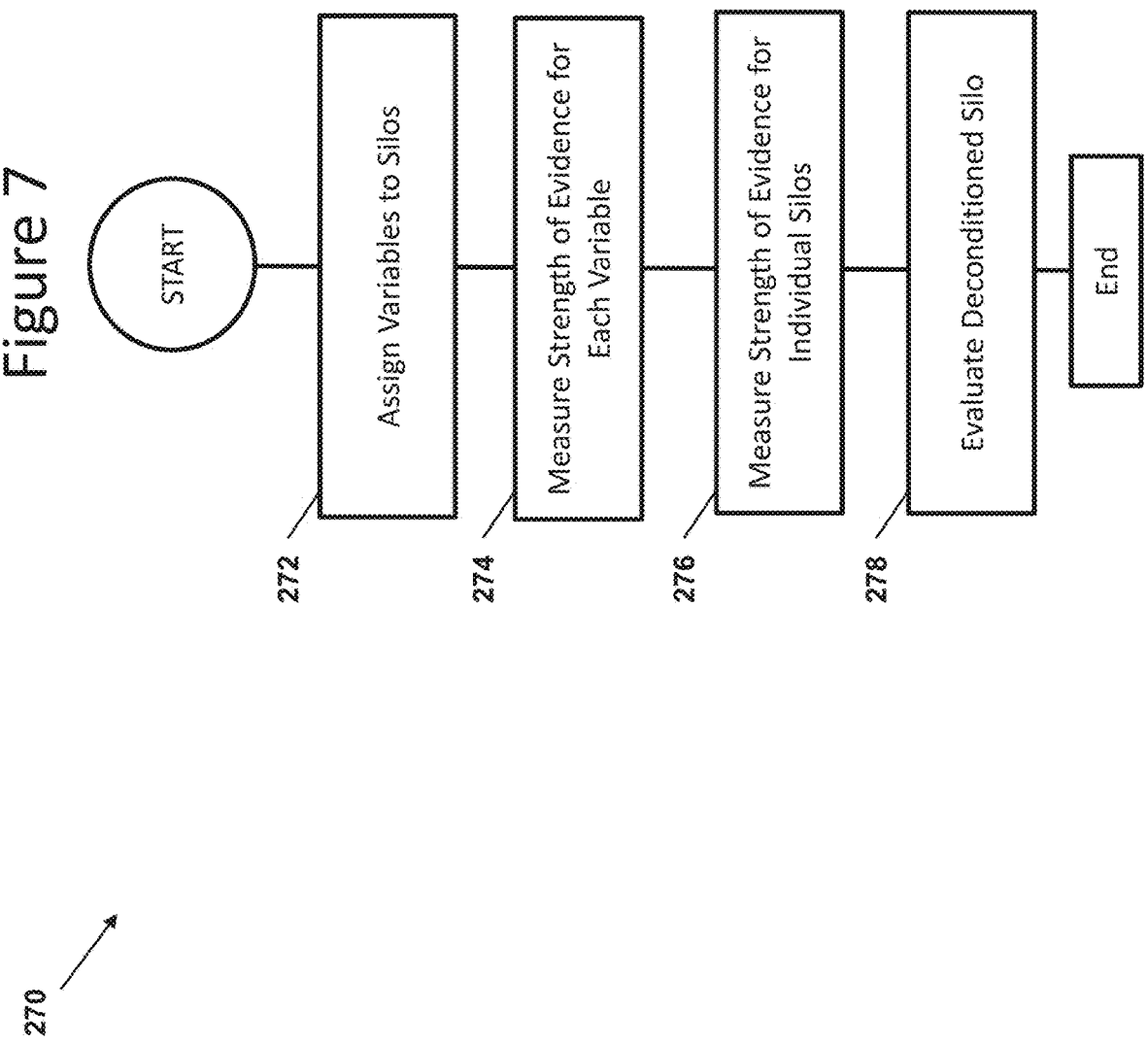
FIG. 7 is a flow chart illustrating another example method of operating the feature extraction engine and the classification engine of FIG. 3.

FIG. 7 is a flow chart illustrating another example method 270 of operating of operating the feature extraction engine 184 and the classification engine 186. The method 270 includes operation 272, 274, and 278.

At operation 272, the variables are assigned to silos. FIG. 10 illustrates a mapping of individual variables that are computed using the raw variables stored in the database 128 for each patient for each test that used in operation 274.

At operation 274, the strength of evidence for each variable is measured. The table in FIG. 11 illustrates example ranges of values used for each variable to determine the likelihood of contribution of that variable to dyspnea. Included in this example table are cut-off points for each variable to determine the likelihood on a scale from 0-3; 0 represents None, 1 represents Slight, 2 represents Moderate, 3 represents Strong. In some embodiments, the example ranges are selected basis of a user or administrator of the gas exchange testing system 100. In some embodiments, the cut-off points are based upon assumptions of worse disease status of the variables mapped for each silo in relation to those values associated with normal individuals, taking also into account age, gender and in some cases Body Mass Index (BMI). In at least some embodiments, the table in FIG. 11 is stored as a configuration file so that the cut-off points can be adjusted to reflect improvements identified by clinical testing of the DR2 system or allow customization.

At operation 276, the strength of evidence for the individual silos is measured. The vertical value of each silo is determined by the choice of variables for the silo in operation 272 and the likeliness computations in operation 274. The numerical value for each variable is determined in operation 274 for all of the variables mapped to the silo in operation 272, summed, and then divided by the number of variables mapped. This produces a value of 0-3, which correlates to the vertical axis labeling in FIG. 8.

In at least some other embodiments, classification is performed using various machine learning and data classification techniques. For example, in at least some embodiments, a classifier is trained for one or more of the chronic disease silos based on measurements captured from both affected and unaffected patients. In at least some embodiments, the classifiers are Bayesian classifiers. In at least some other embodiments, the classifiers are support vector machines. Yet other embodiments of the classifiers are possible as well.

Figure 8:
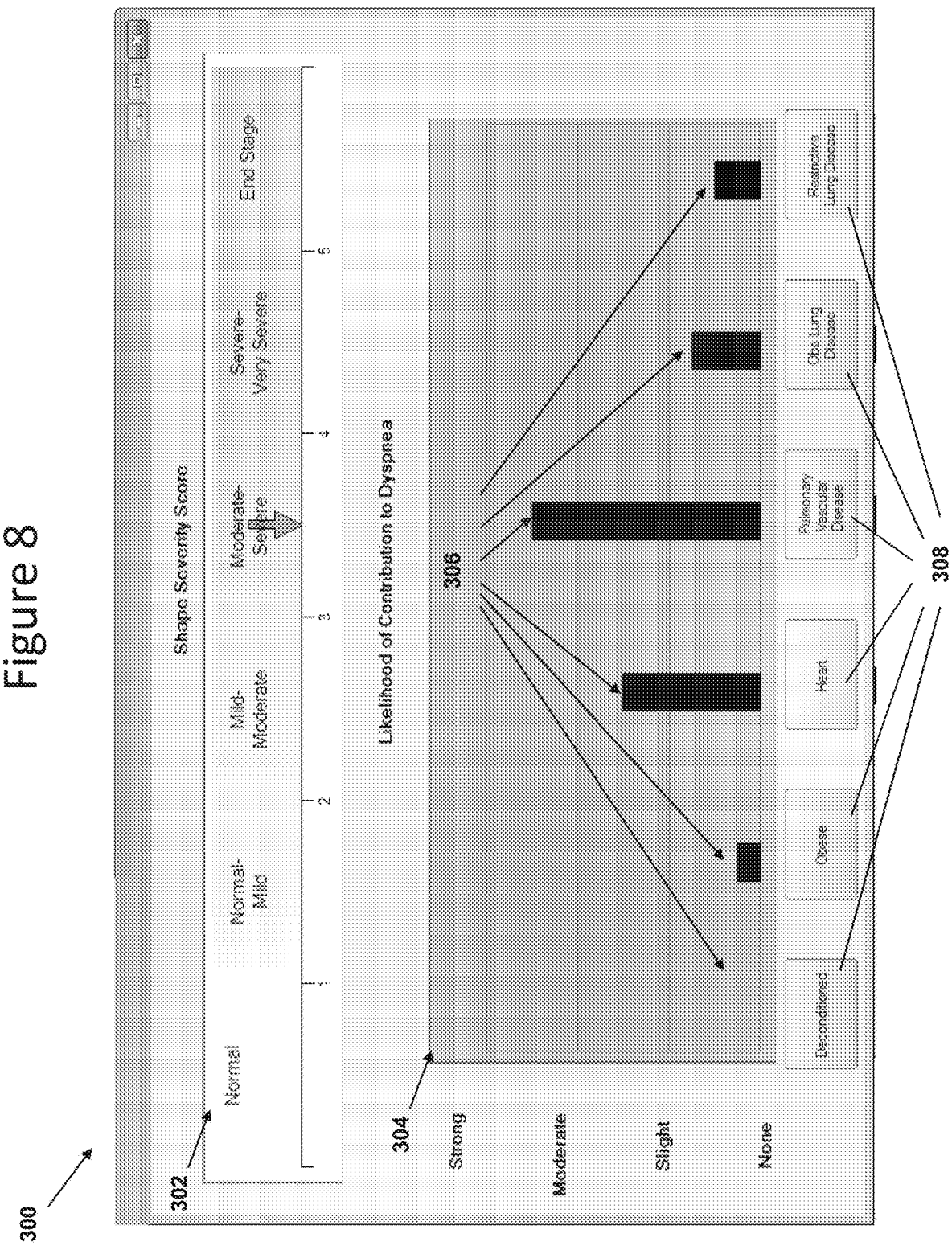
FIG. 8 is an example user interface of the gas exchange testing system of FIG. 1.

FIG. 8 illustrates an example user interface 300 of the gas exchange testing system 100. The user interface 300 includes a disease severity slider 302 and a contribution graph 304. In some embodiments, the user interface 300 is generated by the user interface engine 188.

The disease severity slider 302 indicates the overall severity of the condition of the patient. In some embodiments, the overall severity of the condition is calculated based on data gathered by the data gathering engine 182.

The contribution graph 304 includes one or more silos 306 and one or more pop-up information buttons 308. The silos 306 correspond to the contribution of a particular disease or condition to dyspnea of the patient. In the example shown, there are silos for Deconditioned, Obese, Heart, Pulmonary Vascular Disease, Obstructive Lung Disease, and Restrictive Lung Disease. In some embodiments, the height of the silos is associated with the degree of contribution to dyspnea calculated for the disease or condition. In some embodiments, each of the pop-up information buttons 308 is associated with one of the silos. In some embodiments, the pop-up information buttons 308 are configured to display the measured values and scores of each of the constituent physiological values of the associated silo.

Figure 9:
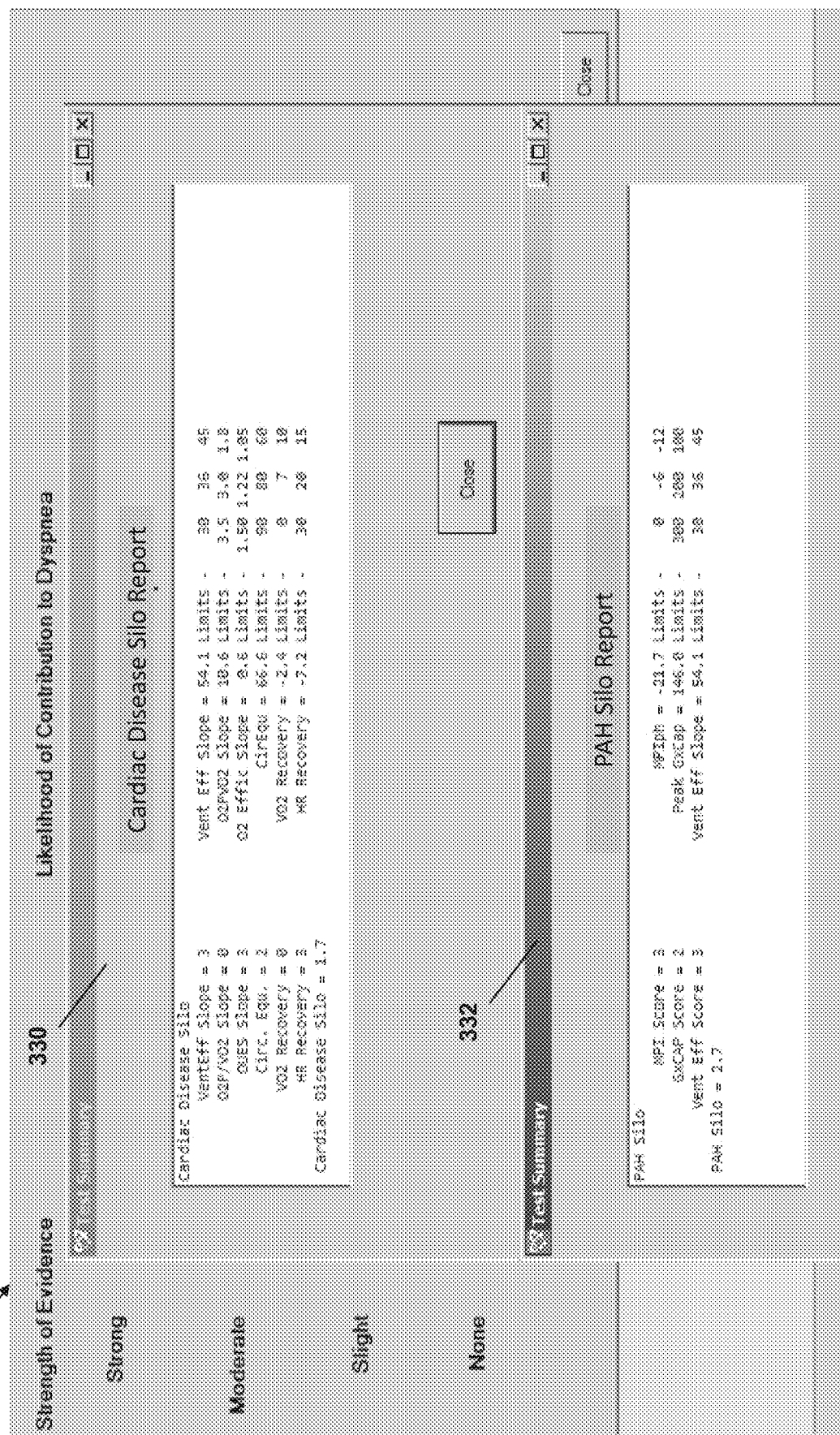
FIG. 9 is another example user interface of the gas exchange testing system of FIG. 1.

FIG. 9 is another illustration of the example user interface 300 of the gas exchange testing system 100. In this example, pop-up information window 330 and pop-up information window 332 are displayed. The pop-up information window 330 displays details used in calculating the contribution of cardiac disease to dyspnea in the patient test data that is shown. Similarly, the pop-up information window 332 displays details used in calculating the contribution of pulmonary arterial hypertension to dyspnea in the patient test data that is shown. Both the pop-up information window 330 and the pop-up information window 332 display the calculated physiological values associated with the silo, the silo scores computed for each of those physiological values, and the limits used to calculate the silo scores. Additionally, both the pop-up information window 330 and the pop-up information window 332 display the contribution value calculated for the silo. In other embodiments, the pop-up information windows include more, less, or different information.

FIG. 10 illustrates an example table 350 that is used in some embodiments of the gas exchange testing system 100 to associate various physiological values with silos. The physiological values are listed in the column 352. The silos are listed in the row 354. In some embodiments, an "X" in table 350 indicates that the gas exchange testing system 100 considers the physiological value listed in column 352 when calculating the contribution score of the silo listed in row 354. Some embodiments include more, fewer, or different silos or physiological values. Further, some embodiments use other techniques to organize and store the data that associates physiological values with silos.

FIG. 11 illustrates an example table 380 that is used in some embodiments of the gas exchange testing system 100 to calculate silo scores for various physiological values. The table comprises a pluralities of rows 382. Each of the rows 382 corresponds to a physiological value. Each row includes a description column 384, a low cut-off value column 386, a medium cut-off value column 388, a high cut-off value column 390, and a silo column 392. The description column 384 stores a description of the physiological value. The low cut-off value column 386, medium cut-off value column 388, and the high cut-off value column 390 store cut-off values that are used in calculating the silo scores for the silo specified in the silo column 392. In some embodiments, the cut-off values are numeric value. In other embodiments, the cut-off values are binary values or other types of values.

In some embodiments, the silo score is calculated by comparing the calculated physiological value for a patient to the cut-off values. If the calculated physiological value for the patient is outside (i.e., greater than or less than, depending on the physiological value) the low cut-off value, a silo score of 0 is assigned. If the calculated physiological value for the patient is between the low cut-off value and the medium cut-off value, a silo score of 1 is assigned. If the calculated physiological value for the patient is between the medium cut-off value and the high cut-off value, a silo score of 2 is assigned. If the calculated physiological value for the patient is outside (i.e., greater than or less than, depending on the physiological value) the high cut-off value, a silo score of 3 is assigned.

Figure 12:
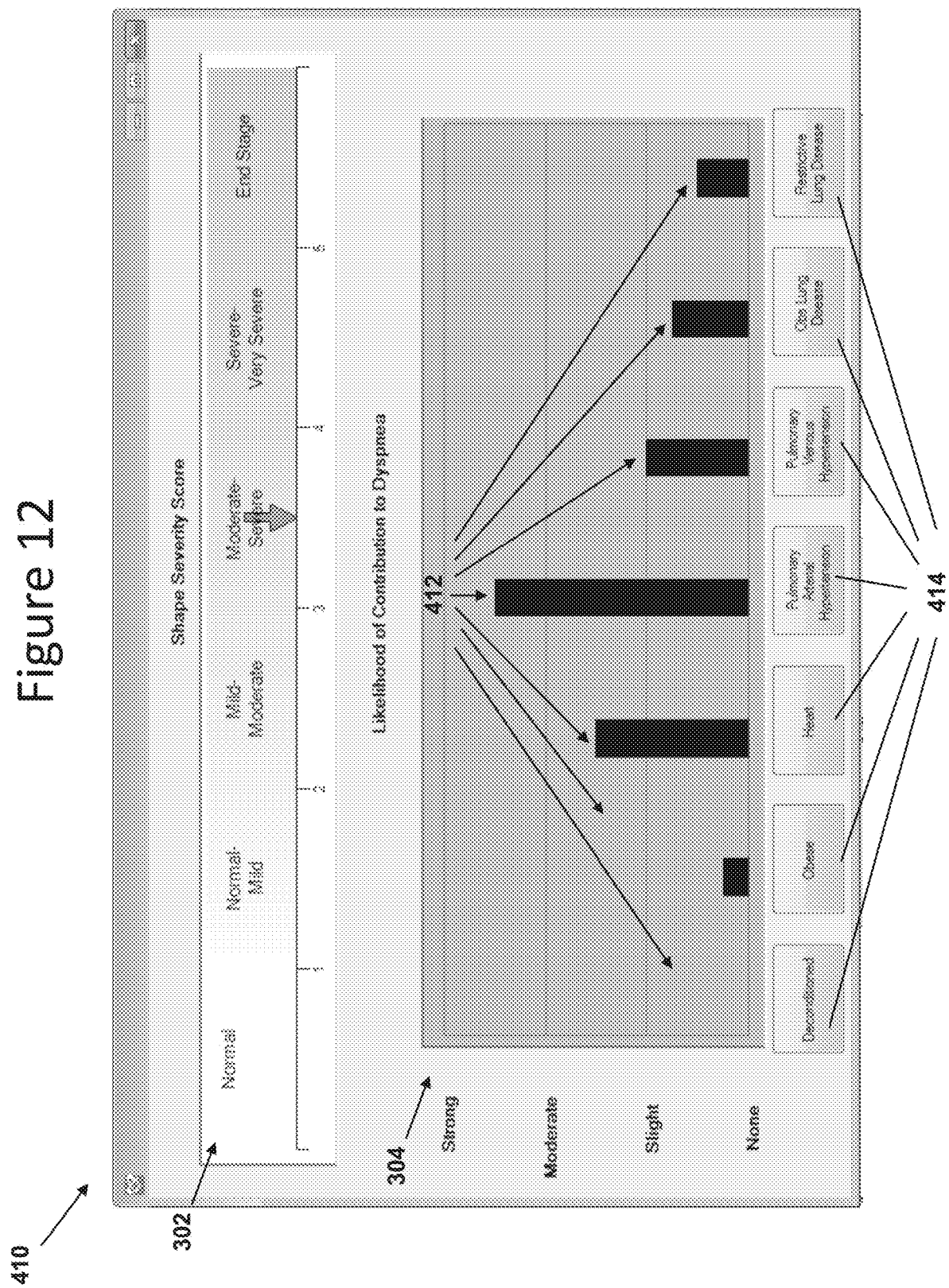
FIG. 12 illustrates another user interface of the gas exchange testing system of FIG. 1 that includes silo splitting.

FIG. 12 illustrates another user interface 410 of the gas exchange testing system 100. The user interface 410 includes the disease severity slider 302 and the contribution graph 304. The contribution graph 304 includes one or more silos 412 and one or more pop-up information buttons 414. The silos 412 are similar to the silos 306, except that the Pulmonary Vascular Disease silo is split into Pulmonary Arterial Hypertension and Pulmonary Venous Hypertension silos. The pop-up information buttons 414 are similar to the pop-up information buttons 308, except that they correspond to the silos 412.

In some embodiments, the disease silos are split or subdivided into multiple silos representing subclasses of the main disease silo. For example, some embodiments include a disease silo titled "Lung Disease" and two subclass silos, Obstructive Lung Disease and Restrictive Lung Disease. Other embodiments are possible as well.

In some embodiments, the user interface 410 is configured to split certain main disease silos by default. In other embodiments, a main disease silo is split only when its contribution value exceeds a predefined threshold. Further, in some embodiments, a main disease silo is split based on user input (e.g., clicking on a "split" button). Other embodiments are possible as well.

As clinical research advances, further "silo splitting" can be implemented. For example, the Pulmonary Arterial Hypertension silo could be further split between WHO 1 and WHO2/3 PH based on various gas exchange variables. For example, some embodiments use separate indexes that relate to heart failure and pulmonary hypertension as Cartesian coordinates to differentiate between WHO 1 and WHO 2/3 PH patients.

Additionally, in some embodiments, the heart silo is split into systolic heart disease and diastolic heart disease. Systolic and diastolic heart disease have different etiologies. Systolic disease is caused by poor cardiac perfusion or CAD (coronary artery disease). In contrast, diastolic disease is caused by the effects of undetected or ineffectively treated systemic hypertension which increases cardiac afterload and stiffens the left ventricle, reducing filling during the relaxation of the heart's cycle, thus reducing output or stroke volume per beat.

The ejection fraction (EF) of the left ventricle is the percent of blood ejected relative to the total amount of blood in the ventricle at the end of the diastolic filling phase. EF is typically less the 45% in systolic heart disease. In contrast, with diastolic heart disease, EF can be normal. This is referred to as heart disease or heart failure with preserved ejection fraction. EF is typically measured in the clinic or hospital setting at rest by echocardiographic technique or by imaging in the cat lab. Very seldom is its increase with exercise evaluated.

In contrast, exercise gas exchange provides a dynamic picture of cardiopulmonary changes during exertion with substantially greater volumes of blood passing through the heart (volume load) during each cardiac cycle. It is known that the EF increases from its resting values during exercise and usually plateaus at the anaerobic threshold, a point during exercise detected by changes in gas exchange variables. A low oxygen pulse (O2P) at this point relative to oxygen uptake or other gas exchange variables can be descriptive of systolic heart disease, with a continued flattening or decrease of its pattern with further cardiac exercise burden.

Systolic heart disease or CAD can show electrocardiographic changes using classical twelve channel ECG ST segment analysis indicative of cardiac ischemia in certain locations of the heart which occur due to inadequate perfusion during incremental exertion. Both systolic and diastolic forms of heart disease are the main causes of heart failure and share similar fates. Both types of heart disease reduce breathing efficiency and alter/blunt the end tidal $CO_2$ ($ETCO_2$) response during exercise. Systolic heart disease or CAD also reduces the contractile motion of the heart and can be detected by abnormal profiles of the O2P relative to oxygen.

In comparison, diastolic dysfunction is likely depicted by lower peak attained O2P but normal patterns descriptive of normal contractile function. Detailed analysis of the O2P pattern during exercise using multiple descriptors of the O2P profile, in conjunction with the MPIph metric is believed to differentiate systolic from diastolic heart disease. It is also believed that the initial filling of the stiff ventricle with diastolic function causes a delay in the increase of the O2P and ETCO2 rise. Likewise, in diastolic heart disease, the O2P is more apt to become flat during exercise, with a threshold being reached in ventricular distensability and filling. It is also likely that the O2P briefly rises during recovery with a reduction in afterload, more so in diastolic vs. systolic disease. A heart with diastolic dysfunction may also demonstrate a slower rate of decrease or decay kinetics during recovery, as compared to a heart with systolic disease.

Additionally, in some embodiments, the heart silo is further split into an additional silo representing Acute Decompensated Heart Failure (ADHF). The ADHF silo can be based on a plurality of physiological measurements. For example, the silo score for the ADHF silo can be based on at least two physiological parameters selected from the group of physiological parameters consisting of: periodic breathing, spirometry measurements, ventilatory efficiency, end tidal CO2, V/Q ratio, pulmonary capacitance, and PetCO2/RR. In embodiments of the system that are connected over a network for remote monitoring or home-based monitoring (such as in FIG. 18), variables associated with ADHF can be used as previously defined to indicate the likelihood of dyspnea caused by the decompensation process.

DR2 Plots

As described previously, FIG. 8 illustrates one method for displaying the disease silos. As was also described previously, FIG. 12 illustrates how the method can be extended to subclasses of disease. In this example, the Pulmonary Vascular Disease silo is split into separate silos for Pulmonary Arterial Hypertension (WHO 1) and Pulmonary Venous Hypertension (WHO 2). In some embodiments, subclass differentiation employs a multi-tiered approach utilizing one or more of (1) mean ranges for select gas exchange variables that have proven to be significantly different between WHO 1 and WHO 2, (2) supportive likelihood data from other disease silos to confirm whether cardiac or lung disease is present, and (3) quadrant graph analysis using an MVI vs MPIph plot (FIG. 13).

Figure 13:
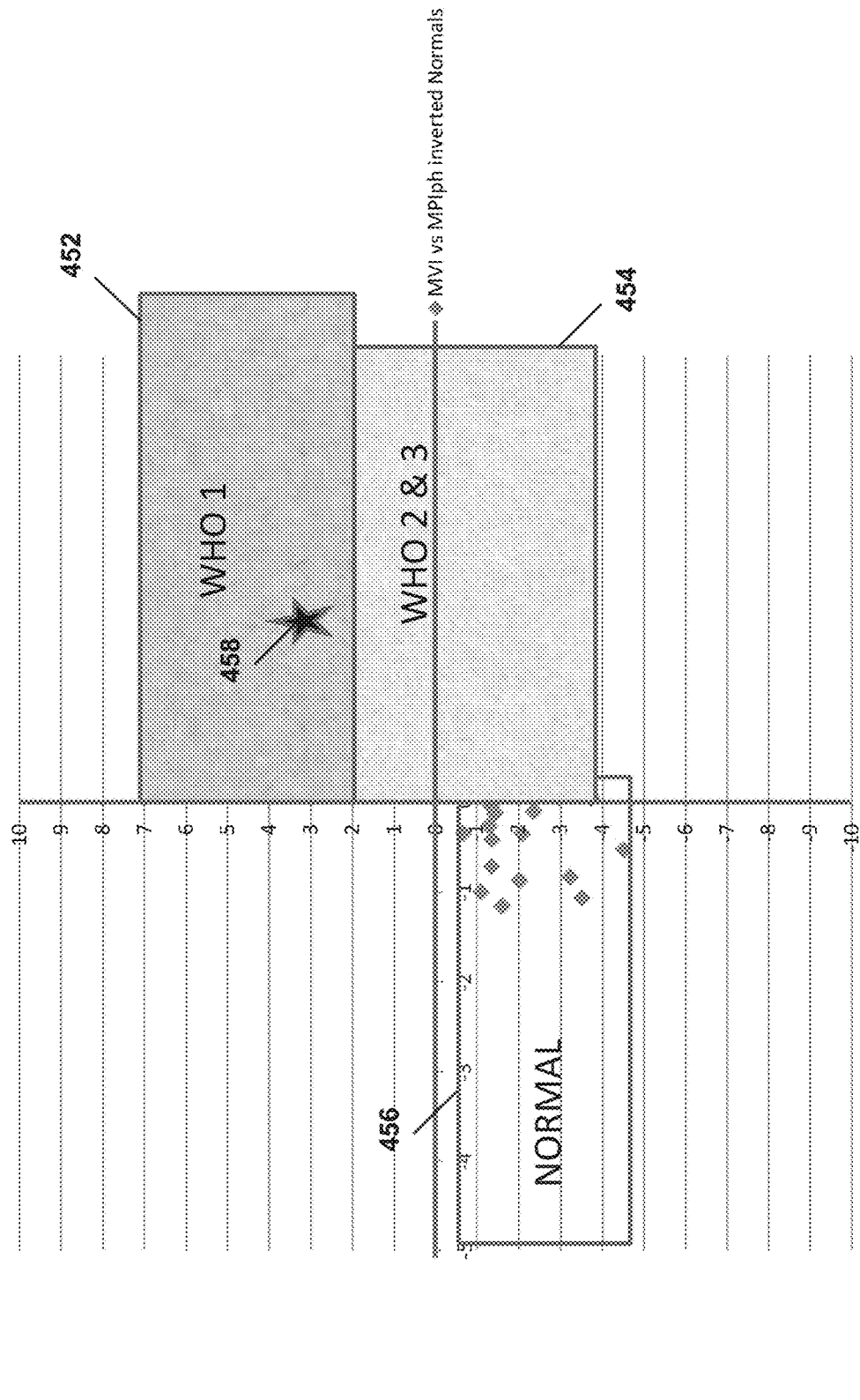
FIG. 13 illustrates an example graph used by some embodiments of the gas exchange test system of FIG. 1 that is used for differentiating between types of pulmonary hypertension.

FIG. 13 illustrates an example graph 450 of some embodiments of the gas exchange testing system 100. The graph 450 includes a WHO 1 region 452, a WHO 2 & 3 region 454, and a normal region 456. Also displayed is an indicator 458 that indicates the position of a test of the patient on the graph 450.

The WHO 1 region 452 indicates a region of the graph 450 that is associated with individuals with WHO 1 PH. The WHO 2 & 3 region 454 indicates a region of the graph 450 that is associated with individuals with WHO 2 & 3 PH. The normal region 456 indicates a region of the graph 450 that is associated with normal, disease free individuals.

In some embodiments, after a patient test is completed, the indicator 458 is plotted on the graph 450 at location corresponding to the MVI (horizontal) and MPIph (vertical) calculated during the test. In FIG. 13, the indicator 458 is located in a region associated with either WHO 1 or WHO 2/3. In this case, the other differentiation tiers are utilized to make the differentiation.

For example, if the likelihood of cardiac disease is moderate to high, secondary PH or WHO 2 is likely present, as compared to WHO 1 without left ventricular dysfunction being present. Similarly, if the flow volume loop performed during FVL phase 212 is supportive of COPD being present, there is increased likelihood that type of PH is relative to WHO class 3 or secondary to lung disease. In addition, the DR2 data would show a reduced or minimal/absence of any cardiac disease being present.

In some embodiments, in order to be consistent with the scaling utilized for MVI (<1 normal, 1 to 4 range of increasing disease severity), the MPIph is scaled to map to the same range of numeric values as the MVI score. For example, in some embodiments, when used for the DR2 system the MPIph value is inverted and normalized calculated using the following formula: inverted and normalized MPIph=(−1*MPIph)/8.

In some embodiments, the regions are defined based on expert knowledge and are configurable. For example, in some embodiments, the dimensions of the regions are derived from either visual observation or statistical determination of data from retrospective analysis of tests on patients with classified disease(s). In some embodiments, the dimensions are stored in a configuration file to enable customization and refinement over time. In other embodiments, the regions are defined using machine learning techniques that analyze a set of training date (e.g., example data from individuals from each of the groups).

Therapy Tracking Using MVI vs MPIph Plot

Figure 14:
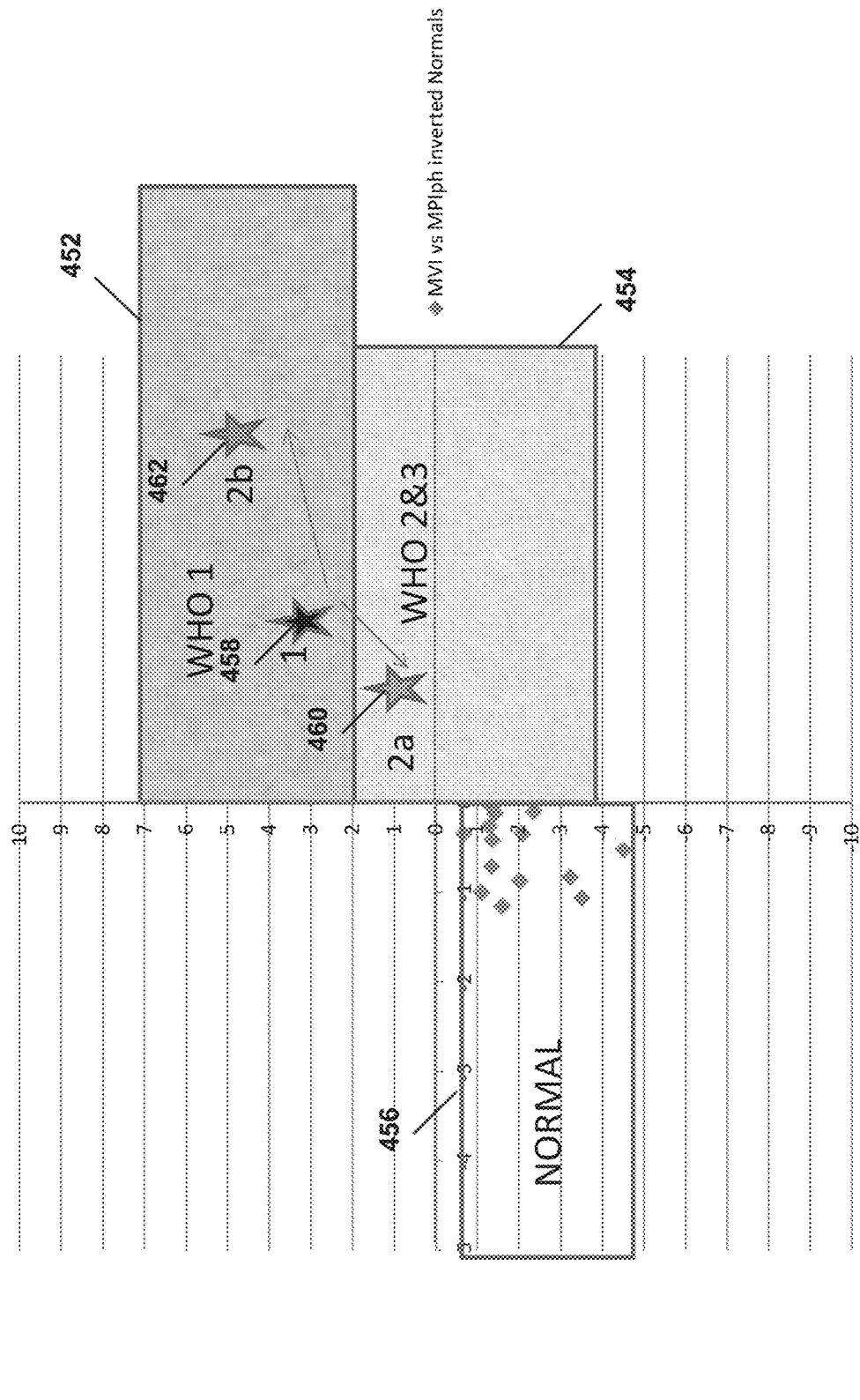
FIG. 14 illustrates an example graph used by some embodiments of the gas exchange test system of FIG. 1 that is used to track changes associated with pulmonary hypertension.

FIG. 14 is another illustration of the example graph 450 of some embodiments of the gas exchange testing system 100. In FIG. 14, the DR2 system is used to observe whether therapy chosen for a patient is producing an improvement or is worsening by observing where the MVI and MPIph (or the inverted and normalized MPIph) from a new test is placed in relation to the preceding test (FIG. 13). If the condition is improving, reductions in either will result in placing a second indicator 460 closer to the normal cluster in the lower left quadrant of the MVI vs MPIph (or the inverted and normalized MPIph) plot. If the patient's condition is worsening, the second indicator 462 will be placed upward and/or to the right on the same plot. In some embodiments, the second indicator is colored green if the patient's condition is improved, and it is colored red if the condition is worsened.

Therapy Tracking Using DR2 Disease Silos

Figure 15:
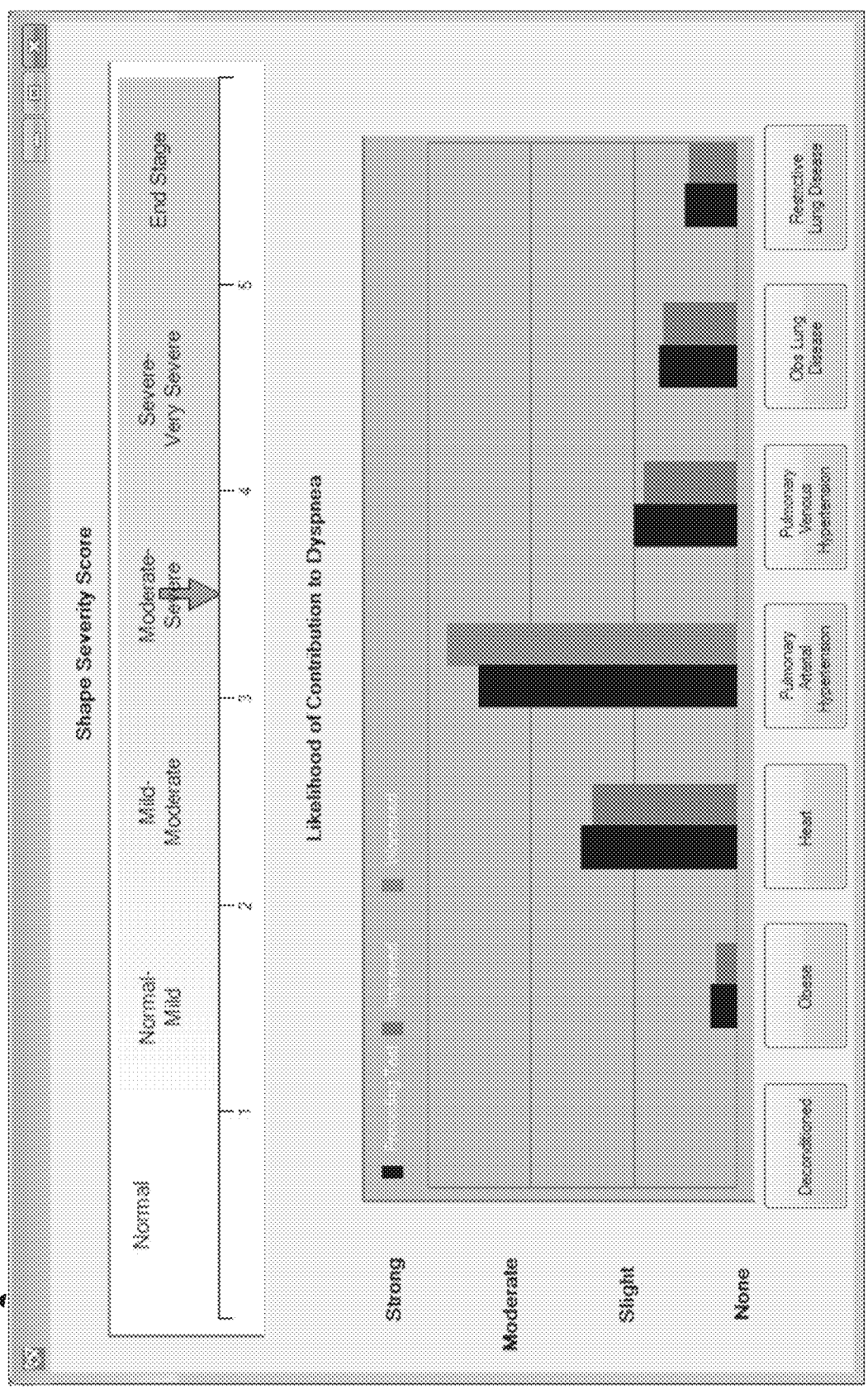
FIG. 15 illustrates a user interface of some embodiments of the gas exchange testing system of FIG. 1 for tracking therapy.

Referring now to FIG. 15, a user interface 490 of some embodiments of the gas exchange testing system 100 is illustrated. The user interface 490 is similar to the user interface 410 (shown in FIG. 12), except that it includes therapy tracking information. In some embodiments, the vertical columns representing the silos for each of the diseases or conditions is split into two columns, each having a width of one half of the width of the column of the original test. The black column represent the values determined in the test previous to the current test. The second half of each of the vertical columns is the value for each silo determined in the current test. In some embodiments, the second half is green if improved (e.g., a lower contribution score than in the original test), and red if worsened (e.g., a higher contribution value that in the original test). In some embodiments, the columns representing the silos have different colors. Additionally, in some embodiments, the therapy tracking includes more than one prior test to enable serial assessment of the patient.

In this manner, all tests can be easily reviewed by the physician, and for those tests that point to Pulmonary Hypertension, primary or secondary, the physician can quickly classify the type of PH.

Therapy Tracking Using a Multivariate Index that Includes Periodic Breathing

In some embodiments, periodic breathing can be included as a component of an index score that is also based on various other physiological measurements. An index score IS that is calculated by some embodiments of the gas exchange testing system 100 is shown:

$$IS=(W1*IVI1+W2*IVI2+\ldots+Wn*IVIn+Wpb*IVIpb)/(n+1) \quad (1)$$

Where
IVI1-IVIn represents Individual Variable Indexes (IVIs) for n number of measured physiological parameters;
IVIpb represents the Individual Variable Index for periodic breathing;
W1-Wn represents the weighting factors for then number of Individual Variable Indexes; and
Wpb represents the weighting factor for the periodic breathing Individual Variable Index.

In some embodiments, the Individual Variable Index for periodic breathing (IVIpb) is calculated as shown below:

$$IVIpb=((1+((PBmeas-PBnv)/PBd))*-1)+1, \quad (2)$$

Where
PBmeas represents the value for periodic breathing measured or entered;
PBnv is the normal value for periodic breathing; and
PBd is the delta for periodic breathing.

The numeric value for PBmeas may be determined quantitatively or qualitatively. For example, the numeric value for PBmeas may be based on the measured amplitude or period of the periodic breathing in the breath data. These values may be determined using computational analysis of the breath data or by manual inspection. Alternatively, PBmeas may be a qualitative score entered by a caregiver based on a visual inspection of the breath data. In at least some embodiments, PBmeas is a binary value of 0 or 1 indicating the absence or presence, respectively, of periodic breathing.

In at least some embodiments, PBd and PBnv are set based on historical data. PBnv may be set to the standard deviation of a sample of data. Alternatively, PBnv is set to a value indicating the absence of periodic breathing (e.g., 0), while PBnv is set 1. Other embodiments are possible.

Further, equations (1) and (2) are examples that are used in some embodiments. Other embodiments use other equations as well.

Over the course of therapy, the index score (IS) may be recalculated multiple times to monitor disease progression and evaluate the efficacy of various treatments. The multiple scores may be stored in a database at the time of evaluation. The scores can then be retrieved and displayed on a user interface of the gas exchange testing system 100.

Figure 18:
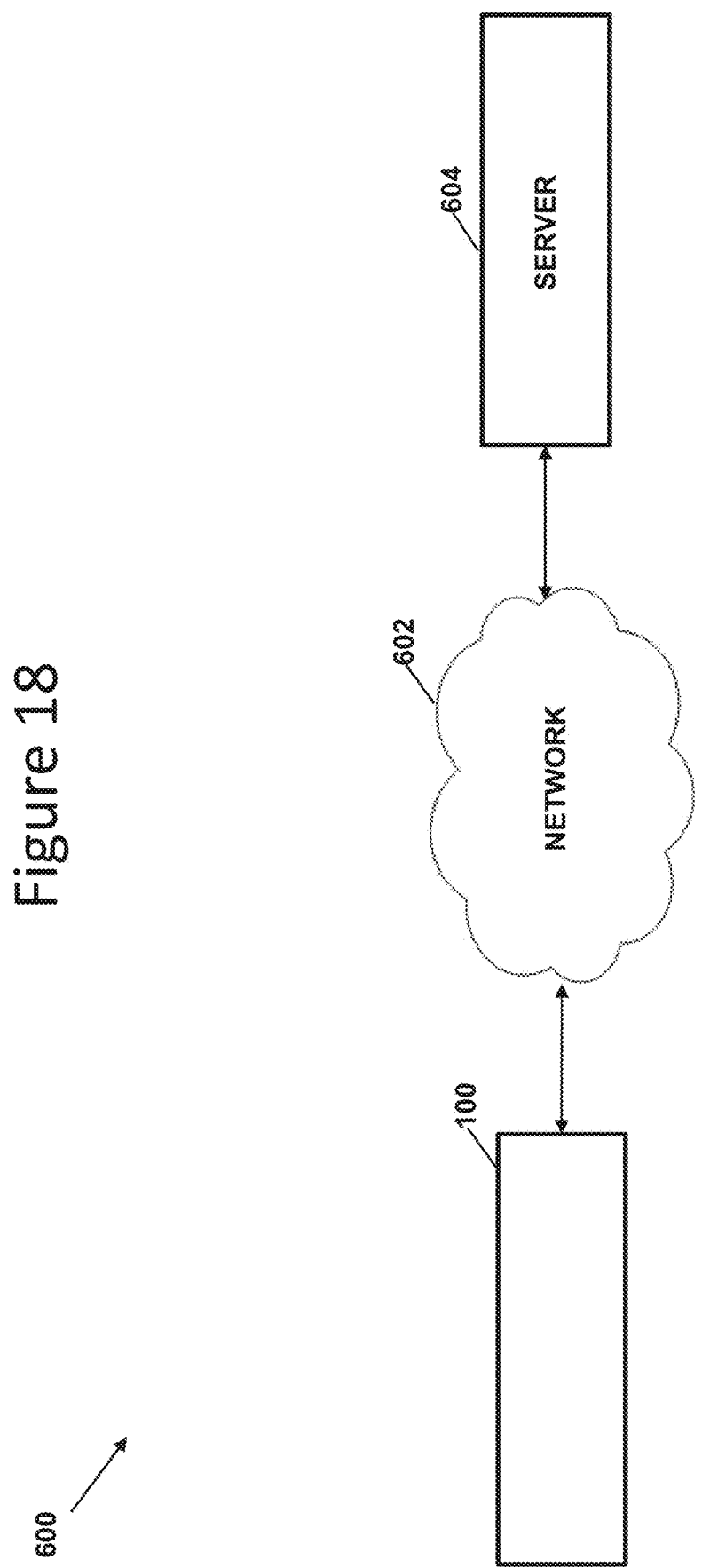
FIG. 18 illustrates an exemplary networked gas exchange testing system.

Referring now to FIG. 18, an exemplary networked gas exchange testing system 600 is illustrated. The networked gas exchange testing system 600 can be used for remote testing and monitoring of patients. For example, the networked gas exchange testing system 600 can be used in non-clinical environments, such as at the patient's home. In this example, the networked gas exchange testing system 600 includes the gas exchange testing system 100, network 602, and server 604.

In some embodiments, the gas exchange testing system 100 is configured to send data associated with gas exchange tests (such as measurements of physiological parameters, index scores, etc.) to the server 604 over the network 602.

The network 602 is an electronic communication network that facilitates communication between the gas exchange testing system 100 and the server 604. An electronic communication network is a set of computing devices and links between the computing devices. The computing devices in the network use the links to enable communication among the computing devices in the network. The network 602 can include routers, switches, mobile access points, bridges, hubs, intrusion detection devices, storage devices, stand-alone server devices, blade server devices, sensors, desktop computers, firewall devices, laptop computers, handheld computers, mobile telephones, and other types of computing devices.

In various embodiments, the network 602 includes various types of links. For example, the network 602 can include wired and/or wireless links, including Bluetooth, ultra-wideband (UWB), 802.11, ZigBee, and other types of wireless links. Furthermore, in various embodiments, the network 602 is implemented at various scales. For example, the network 602 can be implemented as one or more local area networks (LANs), metropolitan area networks, subnets, wide area networks (such as the Internet), or can be implemented at another scale.

The server 604 comprises one or more computing devices. Various embodiments of computing devices have been described above. Further, in some embodiments, the server 604 comprises a single server or a bank of servers. In another example, the server 604 can be a distributed network server, commonly referred to as a "cloud" server.

In some embodiments, the server 604 operates to receive data such as test results and physiological measurements from the gas exchange testing system 100. The server 604 can then process the data and store it in one or more of a database or electronic medical records system. In some embodiments, the server 604 includes pattern recognition system 180.

In some embodiments, the server 604 generates user interfaces, such as with the user interface engine 188, and transmits those user interfaces for display remotely. For example, the server 604 may generate a web page comprising a user interface containing test data transmitted from the gas exchange testing system 100. The web page may then be transmitted to a computing device (e.g., a smart phone, personal computer, or tablet) of the patient or a caregiver.

Additionally, in some embodiments, the gas exchange testing system 100 communicates with a cellular phone or other network-connected computing device to access the network 602. For example, the gas exchange testing system 100 may transmit data to the server 604 via communication with a cell phone using Bluetooth. Other embodiments are possible as well.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method for characterizing contributions of physiological conditions to dyspnea in a patient comprising:
    receiving heart rate data and gas exchange measurements, wherein the gas exchange measurements are based on breath-by-breath data captured during a gas exchange test on a patient, the gas exchange test including an exercise phase during which the patient performs exercise;
    determining a plurality of contribution values that are each associated with a different physiological condition, wherein the plurality of contribution values are numeric values based on the gas exchange measurements captured on the breath-by-breath basis during the exercise phase, wherein at least one of the contribution values is based on the gas exchange data and the heart rate data and each of the plurality of contribution values corresponds to a strength of evidence that the associated physiological condition contributes to dyspnea in the patient wherein the determining a plurality of contribution values includes using a machine learning classifier to determine at least one of the contribution values; and
    outputting the plurality of contribution values to indicate the strength of evidence of the associated physiological conditions.

2. The method of claim 1, wherein the gas exchange test includes a rest phase that precedes the exercise phase and a recovery phase that follows the exercise phase.

3. The method of claim 2, wherein at least one contribution value of the plurality of contribution values is determined based on gas exchange measurements captured on the breath-by-breath basis during a rest phase and the exercise phase.

4. The method of claim 2, wherein at least one contribution value of the plurality of contribution values is determined based on gas exchange measurements captured on the breath-by-breath basis during the recovery phase and the exercise phase.

5. The method of claim 1, wherein the receiving heart rate data and gas exchange measurements includes receiving heart rate data and gas exchange measurements based on breath-by-breath data captured by a flow sensor and an analyzer.

6. The method of claim 1, further comprising repeatedly evaluating one or more of a respiratory exchange rate based on the received gas exchange measurements and a heart rate based on the received heart rate data on a breath-by-breath basis to determine when a predetermined target metric corresponding to exertion level is reached.

7. The method of claim 1, further comprising receiving spirometric measurements including at least one of forced vital capacity (FVC), forced expiratory volume in one second (FEV1), and inspiratory capacity (IC).

8. The method of claim 7, further comprising determining an FEV1/FVC ratio and determining a contribution value associated with obstructed or restrictive lung disease based on the FEV1/FVC ratio.

9. The method of claim 1, wherein the physiological conditions associated with the plurality of contribution values are selected from a group of physiological conditions consisting of heart failure, pulmonary arterial hypertension, pulmonary venous hypertension, obstructed lung, restricted lung, obesity, general deconditioning, and acute decompensated heart failure.

10. The method of claim 1, further comprising generating a user interface that includes a first visual indicator, wherein a property of the first visual indicator is determined based on a first contribution value of the plurality of contribution values.

11. The method of claim 10, wherein the user interface includes a second visual indicator, wherein a property of the second visual indicator is based on a second contribution value of the plurality of contribution values.

12. The method of claim 11, wherein the properties of the first and second visual indicators are selected from a group of properties consisting of:
    height; and
    color.

13. The method of claim 10, wherein the user interface further includes at least one historical visual indicator, wherein a property of the at least one historical visual indicator is determined based on a historical contribution value from a historical gas exchange test of the patient.

14. The method of claim 1,
wherein the receiving heart rate data and gas exchange measurements includes:
performing, using a cardiopulmonary exercise gas exchange analyzer, the gas exchange test on the patient; and
obtaining a plurality of gas exchange measurements, including end tidal CO2, on a breath-by-breath basis during the gas exchange test;
wherein the determining a plurality of contribution values includes:
determining a first contribution value associated with a first physiological condition, wherein the first contribution value is based on at least two of the plurality of gas exchange measurements; and
determining a second contribution value associated with a second physiological condition, wherein the second contribution value is based on at least one of the plurality of gas exchange measurements; and
wherein the outputting the plurality of contribution values includes:
causing the first contribution value and the second contribution value to be displayed.

15. The method of claim 14, wherein causing the first contribution value and the second contribution value to be displayed includes generating a user interface having a first visual indicator and a second visual indicator, wherein a property of the first visual indicator is determined based on the first contribution value and a property of the second visual indicator is determined based on the second contribution value.

16. The method of claim 15, further comprising retrieving historical test data relating to a previous gas exchange test on the patient; and wherein the user interface includes a first historical visual indicator and a second historical visual indicator, wherein a property of the first historical visual indicator is determined based on a first historical contribution value and a property of the second historical visual indicator is determined based on a second historical contribution value, the first historical contribution value being associated with the first physiological condition and being based on the historical test data, and the second historical contribution value being associated with the second physiological condition and being based on the historical test data.

17. The method of claim 14, wherein the first physiological condition and the second physiological condition are selected from a group of physiological conditions consisting of heart failure, pulmonary arterial hypertension, pulmonary venous hypertension, obstructed lung, restricted lung, obesity, general deconditioning, and acute decompensated heart failure.

18. The method of claim 14, further comprising:
receiving results of a spirometry test on the patient, wherein the spirometry test includes a flow-volume loop;
obtaining a plurality of spirometric measurements, including at least one of forced vital capacity (FVC), inspiratory capacity (IC), and forced expiratory volume in one second (FEV1); and
wherein the determining the second contribution value includes determining the second contribution value based on at least one of the plurality of spirometric measurements and the at least one of the plurality of gas exchange measurements.

19. The method of claim 1, further comprising:
obtaining a plurality of spirometric measurements from a spirometry test on a patient, including forced vital capacity (FVC), inspiratory capacity (IC), and forced expiratory volume in one second (FEV1); and
retrieving historical test data relating to a previous gas exchange test on the patient;
wherein the receiving heart rate data and gas exchange measurements includes:
obtaining a plurality of gas exchange measurements, including end tidal CO2, on a breath-by-breath basis during a gas exchange test that includes a rest phase, an exercise phase during which the patient performs exercise, and a recovery period;
wherein the determining a plurality of contribution values includes:
determining a first contribution value associated with a first physiological condition, the first contribution value being based on a first weighted combination of at least one of the plurality of spirometric measurements and at least one of the plurality of gas exchange measurements;
determining a second contribution value associated with a second physiological condition, wherein the second contribution value is based on a second weighted combination of one or more of the plurality of spirometric measurements and at least one of the plurality of gas exchange measurements; and
wherein the outputting the plurality of contribution values includes:
generating a user interface that includes a first visual indicator, a second visual indicator, a third visual indicator, and a fourth visual indicator, a property of the first visual indicator being determined based on the first contribution value, a property of the second visual indicator being determined based on the second contribution value, a property of the third visual indicator being determined based on a first historical contribution value associated with the first physiological condition and being based on the historical test data, and a property of the fourth visual indicator being determined based on a second historical contribution value associated with the second physiological condition and being based on the historical test data.

20. The method of claim 19, further comprising:
performing the spirometry test on the patient using a flow sensor of a cardiopulmonary exercise gas exchange analyzer, wherein the spirometry test includes a flow-volume loop; and
performing, using the cardiopulmonary exercise gas exchange analyzer, the gas exchange test on the patient, wherein the gas exchange test includes an exercise phase during which the patient performs exercise.

21. The method of claim 1, wherein the machine learning classifier includes a Bayesian classifier.

22. The method of claim 1, wherein the machine learning classifier includes a support vector machine.

* * * * *